United States Patent
Munce et al.

(10) Patent No.: US 7,972,272 B2
(45) Date of Patent: Jul. 5, 2011

(54) ELECTROSTATICALLY DRIVEN IMAGE PROBE

(75) Inventors: Nigel Robert Munce, Toronto (CA);
Victor Xiao Dong Yang, Toronto (CA);
Brian Courtney, Toronto (CA);
Amandeep Singh Thind, Toronto (CA)

(73) Assignee: University Health Network, Toronto, ON (CA)

( * ) Notice: Subject to any disclaimer, the term of this patent is extended or adjusted under 35 U.S.C. 154(b) by 678 days.

(21) Appl. No.: 12/010,205

(22) Filed: Jan. 22, 2008

(65) Prior Publication Data

US 2008/0243002 A1 Oct. 2, 2008

Related U.S. Application Data

(60) Provisional application No. 60/881,169, filed on Jan. 19, 2007.

(51) Int. Cl.
*A61B 8/00* (2006.01)
*A61B 5/00* (2006.01)
*G02B 26/10* (2006.01)

(52) U.S. Cl. ............... 600/462; 600/478; 359/199.2

(58) Field of Classification Search .......... 600/444–446, 600/459, 461–471, 473–478; 310/25, 36, 310/309; 359/199.2, 200.6
See application file for complete search history.

(56) References Cited

U.S. PATENT DOCUMENTS

| | | | | |
|---|---|---|---|---|
| 5,321,501 A * | 6/1994 | Swanson et al. | ............... | 356/479 |
| 5,606,975 A | 3/1997 | Liang et al. | ............... | 128/662.06 |
| 5,647,367 A | 7/1997 | Lum et al. | | |
| 5,651,366 A | 7/1997 | Liang et al. | ............... | 128/662.06 |
| 5,771,902 A * | 6/1998 | Lee et al. | ............... | 128/897 |
| 5,779,643 A | 7/1998 | Lum et al. | | |
| 6,294,775 B1 * | 9/2001 | Seibel et al. | ............... | 250/208.1 |
| 6,485,413 B1 * | 11/2002 | Boppart et al. | ............... | 600/160 |
| 6,626,834 B2 | 9/2003 | Dunne et al. | | |
| 6,903,854 B2 * | 6/2005 | Gelikonov et al. | ........ | 359/196.1 |
| 7,077,808 B2 | 7/2006 | Couvillon, Jr. | ............... | 600/466 |
| 7,115,092 B2 | 10/2006 | Park et al. | ............... | 600/143 |
| 7,312,879 B2 * | 12/2007 | Johnston | ............... | 356/614 |
| 7,391,013 B2 * | 6/2008 | Johnston et al. | ............... | 250/234 |
| 7,457,021 B2 * | 11/2008 | Desai | ............... | 359/223.1 |
| 7,616,986 B2 * | 11/2009 | Seibel et al. | ............... | 600/476 |
| 7,680,373 B2 * | 3/2010 | Melville et al. | ............... | 385/33 |
| 2005/0020926 A1 | 1/2005 | Wiklof et al. | | |

OTHER PUBLICATIONS

"The Electronics of a Control System for Micromirrors in a Laser-Scanning Device", Wagner et al, IEEE, 2002, pp. 1207-1210.

* cited by examiner

*Primary Examiner* — Francis Jaworski
(74) *Attorney, Agent, or Firm* — Hill & Schumacher; Lynn C. Schumacher

(57) ABSTRACT

The present invention provides an imaging probe for imaging mammalian tissues and structures using high resolution imaging, including ultrasound and optical coherence tomography. The imaging probe uses electrostatic discharge for actuating a metalized cantilever which holds the end portion of imaging assembly which emits energy in the imaging probe device by holding the cantilever at a potential such that it is neither grounded or charged such that the only electrical path to ground is through a dissipative polymer forming part of the device which is enveloped by a wire or coil held at ground potential. A high voltage electrode attracts the metalized cantilever and the dissipative polymer is used to connect to the cantilever to ground causing the cantilever to move about thereby scanning the region in front of the probe.

22 Claims, 34 Drawing Sheets

ELECTROSTATICALLY DRIVEN IMAGE PROBE

CROSS REFERENCE TO RELATED U.S. APPLICATION

This patent application relates to, and claims the priority benefit from, U.S. Provisional Patent Application Ser. No. 60/881,169 filed on Jan. 19, 2007, in English, entitled IMAGING PROBE, which is incorporated herein by reference in its entirety.

FIELD OF THE INVENTION

The present invention relates generally to the field of imaging mammalian tissues and structures using high resolution imaging, including high frequency ultrasound and optical coherence tomography using electrostatic forces to generate motion of a scanning mechanism which is coupled to ground through a dissipative polymer to thereby scan regions of interest.

BACKGROUND OF THE INVENTION

Forward looking imaging devices for viewing small (1-20 mm) lumens, orifices, and cavities of the body remain a difficult engineering challenge. In many instances, the forward looking imaging geometry is, however, more amenable to providing interventional guidance than convention side-viewing probes. In order to address this challenge we present the use of an electrostatic probe that uses a dissipative polymer to indirectly couple a cantilever to a ground potential.

Boppart et al. (U.S. Pat. No. 6,485,413) describes the use of an electrostatic-based actuator for forward-viewing optical coherence tomography. The Boppart patent discloses a device in which the cantilever is directly connected to ground or enabled with an electrostatic slide. This direct connection to ground of the cantilever is problematic resulting in significant electrostatic discharge given the high voltage necessary to oscillate a rigid fiber.

Other forward-viewing catheter patents of note are Park et al. (U.S. Pat. No. 7,115,092) which describes a forward looking device scanned using shape memory alloys. Liang and Hu (U.S. Pat. Nos. 5,651,366 and 5,606,975 respectively) describe various forward looking ultrasound imaging devices in which ultrasound energy is directed in a forward direction by mechanically moved mirrors.

Couvillon et al. (U.S. Pat. No. 7,077,808) also describe forward viewing ultrasound imaging devices where in the scanning mechanism is an electroactively driven polymer.

It would be very advantageous to provide an imaging device having a scanning mechanism which avoids significant electrostatic discharge.

SUMMARY OF THE INVENTION

The present invention provides a novel imaging probe for ultrasound or optical coherence tomography (OCT) which uses an electrostatic means for actuating a metalized cantilever (which holds the end portion of imaging system which emits energy) in an imaging probe device by holding the metalized cantilever at a potential such that it is neither grounded or charged such that the only electrical path to ground is through a dissipative polymer forming part of the device which is enveloped by a wire or coil held at ground potential. A high voltage electrode attracts the metalized cantilever and the dissipative polymer is used to connect to the cantilever to ground.

The scanning cantilever coupled to an imaging system coupled to the scanning cantilever may be configured for optical coherence tomography, ultrasonic imaging, or confocal imaging.

Tuning the oscillation frequency of the cantilever may be provided by varying the degree to which the dissipative polymer is coupled to ground potential. The oscillation frequency of the cantilever may be varied by increasing or decreasing the driving voltage used to attract the cantilever.

An electrostatic peak voltage obtained by measuring the voltage in the grounding wire wrapped around the dissipative polymer catheter may be used as a triggering means.

Thus, in one embodiment of the present invention there is provided an electrostatically driven imaging probe, comprising:

a) an elongate hollow catheter sheath having distal front and back sections and an elongate proximal section and having a diameter suitable to permit insertion of the elongate hollow catheter sheath into bodily lumens and cavities, the distal back section containing an electrically dissipative polymer sealed therein which is wrapped by a metal coil for connection to ground potential and a timing circuit;

b) imaging means located in said distal front section for emitting energy and receiving energy reflected back from interior surfaces of said bodily lumens and cavities, said distal front section containing one of a medium and vacuum sealed therein which allows transmission of imaging energy emitted by the imaging means, said imaging means being connected to an imaging conduit which extends through a proximal end of the elongate hollow catheter sheath for connection to an image processing and display system, said imaging conduit being enveloped by metal and a portion of the metal enveloped imaging conduit in the distal front section forming a cantilever; and c) an elongate electrode located in the elongate hollow catheter sheath having an elongate uninsulated electrode section located in said front distal section, the elongate electrode being connected to a high voltage power supply, wherein in operation when a high voltage is applied to the elongate electrode the cantilever is electrically attracted to the elongate uninsulated electrode section and undergoes deflection towards the elongate uninsulated electrode section and upon contacting the elongate uninsulated electrode section the portion of the metal enveloped imaging conduit in the distal front section acquires an electrical charge from the elongate uninsulated electrode section thereby causing the metal enveloped imaging conduit in the distal front section to be repelled therefrom thereby causing the imaging means to scan the field of view.

Another embodiment of the present invention provides an electrostatically driven imaging probe, comprising:

a) an elongate hollow catheter sheath having distal front and back sections and an elongate proximal section and having a diameter suitable to permit insertion of the elongate hollow catheter sheath into bodily lumens and cavities, the distal back section containing an electrically dissipative polymer sealed therein which is wrapped by a metal coil which is connected to ground potential and a timing circuit;

b) imaging means located in said distal front section for emitting energy and receiving energy reflected back from interior surfaces of said bodily lumens and cavities, said distal front section containing one of a medium and vacuum sealed therein which is transparent to said energy emitted by the imaging means, said imaging means being connected to an imaging conduit which extends through a proximal end of the elongate hollow catheter sheath for connection to an image processing and display system;

c) a conductive, reflective disc pivotally mounted about a pivot axis in said front distal section and electrically coupled to said electrically dissipative polymer, said reflective member being positioned to receive and reflect said energy from said imaging means, and to receive and reflect said energy reflected back from interior surfaces of said bodily lumens and cavities back to said imaging means;

d) a ground electrode having an uninsulated section located in said distal front section connected to said electrical ground potential; and e) an elongate electrode located in the elongate hollow catheter sheath having an elongate uninsulated electrode section located in said front distal section, the elongate electrode being connected to a high voltage power supply, wherein in operation when a high voltage is applied to the elongate electrode the conductive, reflective disc is electrically attracted to the elongate uninsulated electrode section causing said conductive, reflective disc to pivot about said pivot axis in one direction causing an outer edge off said conductive, reflective disc to tilt towards said elongate electrode and upon contact with said elongate electrode said conductive, reflective disc acquires charge from said elongate electrode causing it to be repelled thereby resulting in the conductive, reflective disc to pivot towards said ground electrode, and upon contact of said conductive, reflective disk with said ground electrode the conductive, reflective disk loses its charge resulting in its ability to once again be attracted to said electrode.

A further understanding of the functional and advantageous aspects of the invention can be realized by reference to the following detailed description and drawings.

BRIEF DESCRIPTION OF THE DRAWINGS

Preferred embodiments of the invention will now be described, by way of example only, with reference to the drawings, in which:

FIG. 24A shows an optical coherence tomography image of a nearly occluded piece of tubing;

FIG. 24B shows a white light photograph of the nearly occluded piece of tubing;

FIG. 24C shows an optical coherence tomography image of a piece of excised rabbit colon;

FIGS. 25A and 25 B show an in vivo optical coherence tomography of a tadpole heart taken with an embodiment of the imaging probe in which a fiber was scanned proximal to a GRIN lens;

FIG. 25A shows a structural image of the tadpole heart;

FIG. 27A shows a sector image taken with an embodiment that scans a ball lens;

FIG. 27B shows a sector image taken with an embodiment of the probe in which a cleaved fiber is scanned proximal to a GRIN lens;

DETAILED DESCRIPTION OF THE INVENTION

Figure 1A:
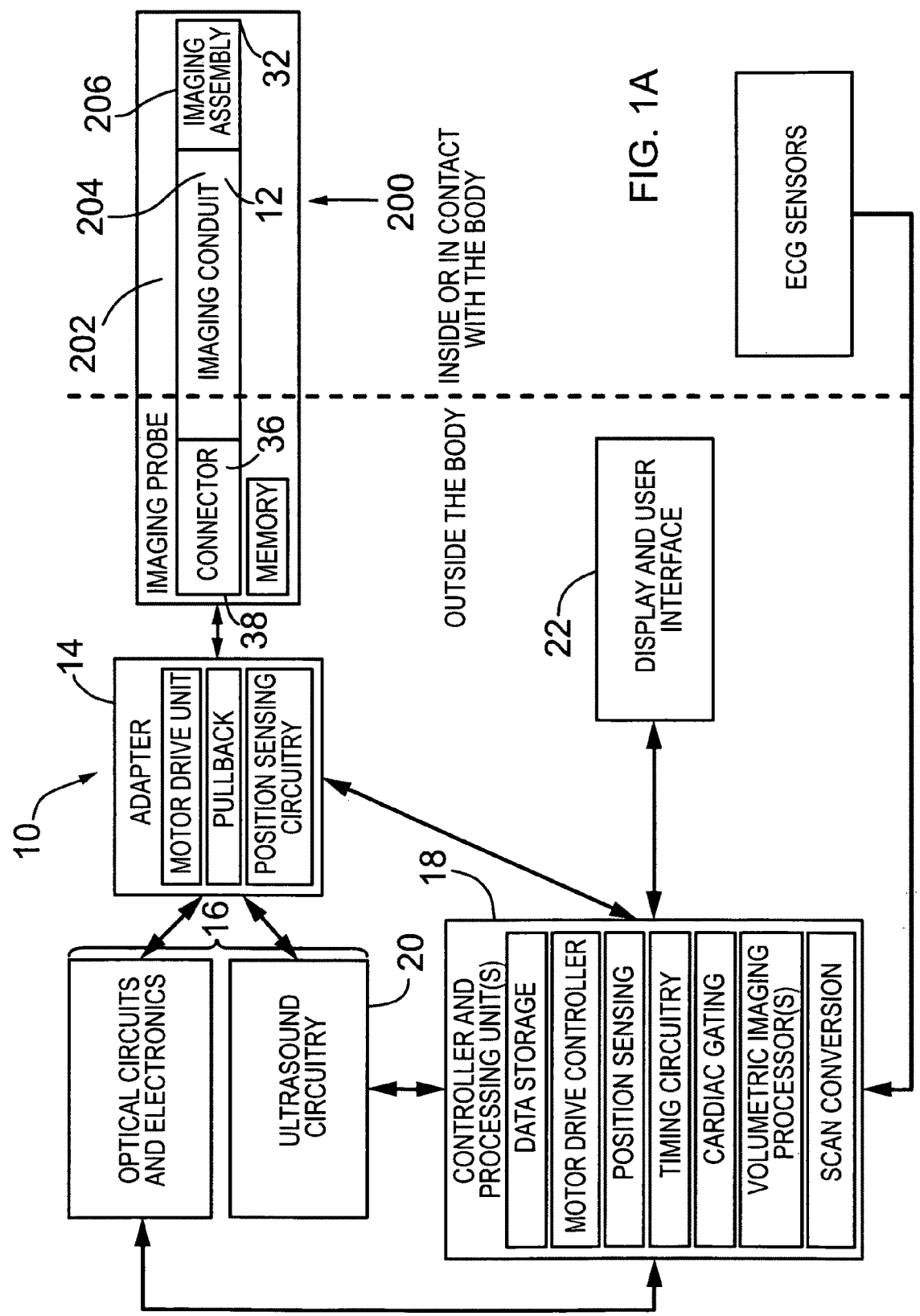
FIG. 1A is a schematic of an imaging system including ultrasound and optical imaging components.

Generally speaking, the systems described herein are directed to an imaging probe using either optical or ultrasonic (or both) imaging. As required, embodiments of the present invention are disclosed herein. However, the disclosed embodiments are merely exemplary, and it should be understood that the invention may be embodied in many various and alternative forms. The Figures are not to scale and some features may be exaggerated or minimized to show details of particular elements while related elements may have been eliminated to prevent obscuring novel aspects. Therefore, specific structural and functional details disclosed herein are not to be interpreted as limiting but merely as a basis for the claims and as a representative basis for teaching one skilled in the art to variously employ the present invention. For purposes of teaching and not limitation, the illustrated embodiments are directed to an imaging probe.

As used herein, the terms "about", and "approximately" when used in conjunction with ranges of dimensions, temperatures or other physical properties or characteristics is meant to cover slight variations that may exist in the upper and lower limits of the ranges of dimensions so as to not exclude embodiments where on average most of the dimensions are satisfied but where statistically dimensions may exist outside this region. For example, in embodiments of the present invention dimensions of components of the imaging probe are given but it will be understood that these are not meant to be limiting.

Generally, in the several embodiments of the present invention that enable forward looking imaging with a cantilever based imaging assembly; the principal of electrostatic dissipative polymers is used advantageously in order to create an oscillatory motion and/or to prevent electrostatic discharge. While direct connection of the cantilever to an electrical field such that the cantilever is held at ground/potential and an electrode within the catheter is held at a potential/ground, will cause motion of the cantilever as described in prior art, the present invention describes herein a configuration which includes coupling of the cantilever to a dissipative polymer. As discussed hereinafter, it is possible to cause the cantilever to move continuously in an oscillatory motion with the application of a high constant voltage, low current field when coupling a dissipative polymer between a metalized cantilever and the ground potential. The use of the probe with two electrodes in which motion is driven by turning individual electrodes either on or off or driven by providing different driving signals to each electrode is also described. In these cases the use of a dissipative polymer eliminates the direct connection to ground potential and hence limits the chance of electrical discharge.

The embodiments shown in FIGS. 1B to 21 and 28 use electrostatic actuation in order to move a cantilever. FIG. 29 to 32 describe an embodiment in which electrostatic actuation is used to move a reflecting disk. In all the drawings the source of the field is marked as "HV". A high voltage power source with a low current (3 to 100 microamperes) has been used in the embodiments described hereinafter. However, those skilled in the art will understand that a high voltage amplifier may be used with a function generator as well as high voltage, high current sources.

FIG. 1A represents an overview of an exemplary imaging system constructed in accordance with the present invention shown generally at 10. It comprises an electrostatically driven imaging probe 200, which connects via an adapter 14 to an image processing and display system 16. The image processing and display system 16 comprises the necessary hardware to support one or more of the following imaging modalities: 1) ultrasound, 2) optical coherence tomography, 3) angioscopy, 4) infrared imaging, 5) near infrared imaging, 6) Raman spectroscopy-based imaging and 7) fluorescence imaging.

The system herein described further typically comprises a controller and processing unit 18 to facilitate the coordinated activity of the many functional units of the system, and may further comprise a display and/or user interface and may further comprise electrode sensors to acquire electrocardiogram signals from the body of the patient being imaged. The electrocardiogram signals may be used to time the acquisition of imaging data in situations where cardiac motion may have an impact on image quality.

The optical circuits and electronics forming image processing and display system 16, if included in a particular implementation of the present invention, may include any or all of the following components: interferometer components, one or more optical reference arms, optical multiplexors, optical demultiplexors, light sources, photodetectors, spectrometers, polarization filters, polarization controllers, timing circuitry, analog to digital converters and other components known to facilitate any of the optical imaging techniques described in the background and prior art sections. The ultrasound circuitry 20 may include any or all of the following components: pulse generators, electronic filters, analog to digital converters, parallel processing arrays, envelope detection, amplifiers including time gain compensation amplifiers and other components known to facilitate any of the acoustic imaging techniques described in the background and prior art sections.

The controller and processing units 18, if included in a particular implementation of the present invention, serve multiple purposes and the components would be markedly adapted based on the needs of a particular imaging system. It could include one or a combination of motor drive controller, data storage components (such as memory, hard drives, removable storage devices, readers and recorders for portable storage media such as CDs and DVDs), position sensing circuitry, timing circuitry, cardiac gating functionality, volumetric imaging processors, scan converters and others. A display and user interface 20 is also optionally provided for either real time display or display of data at a time later than the time at which imaging data is acquired.

The imaging probe 200 comprises an imaging means 206 in the distal front section, an imaging conduit 204 and a connector 36 at the back of the sheath 202. The imaging means 206 is located at the distal end of a catheter for the purpose of scanning optical or ultrasonic energy in front of the catheter to examine tissue located either inside or on the surface of the human body. The imaging conduit 204 serves to transfer the information obtained from the scanned beam to either optical circuits and electronics or ultrasound electronics 20 outside of the imaging probe 200. The imaging probe 200 will be discussed in more detail below, but it may comprise an optical fiber or an ultrasound transducer with associated coaxial cable in the imaging conduit 204.

The adapter 14 facilitates transmission of signals within any fibers and/or wires to the appropriate image processing units. The adapter 14 may also incorporate a pullback mechanism or a reciprocating push-pull mechanism to facilitate longitudinal translation of the imaging assembly. Such longitudinal translation of the imaging assembly may occur in conjunction with the longitudinal translation of an external shaft that surrounds the imaging conduit 204, or may occur within a relatively stationary external shaft. Additional sensors may be incorporated as part of the adapter 14, such as position sensing circuitry, for example to sense the angle of rotation of a rotary component within the imaging probe 200.

The imaging probe 200 may also include a memory component such as an EEPROM or other programmable memory device that includes information regarding the imaging probe 200 to the rest of the imaging system. For example, it may include specifications regarding the identification of specifications of the imaging probe 200 and may also include calibration information regarding the probe 200.

Also included in the adaptor 14 is the possibility of a coupling means such as a fiber optic rotary joint and/or an electrical slip ring (not shown) to allow the imaging conduit 204 to be rotated while maintaining structural fidelity. This adaptor 14 may also provide a coupling means to the connector 36 such that a rotational torque may be applied to the imaging probe causing the probe to rotate.

Figure 1B:
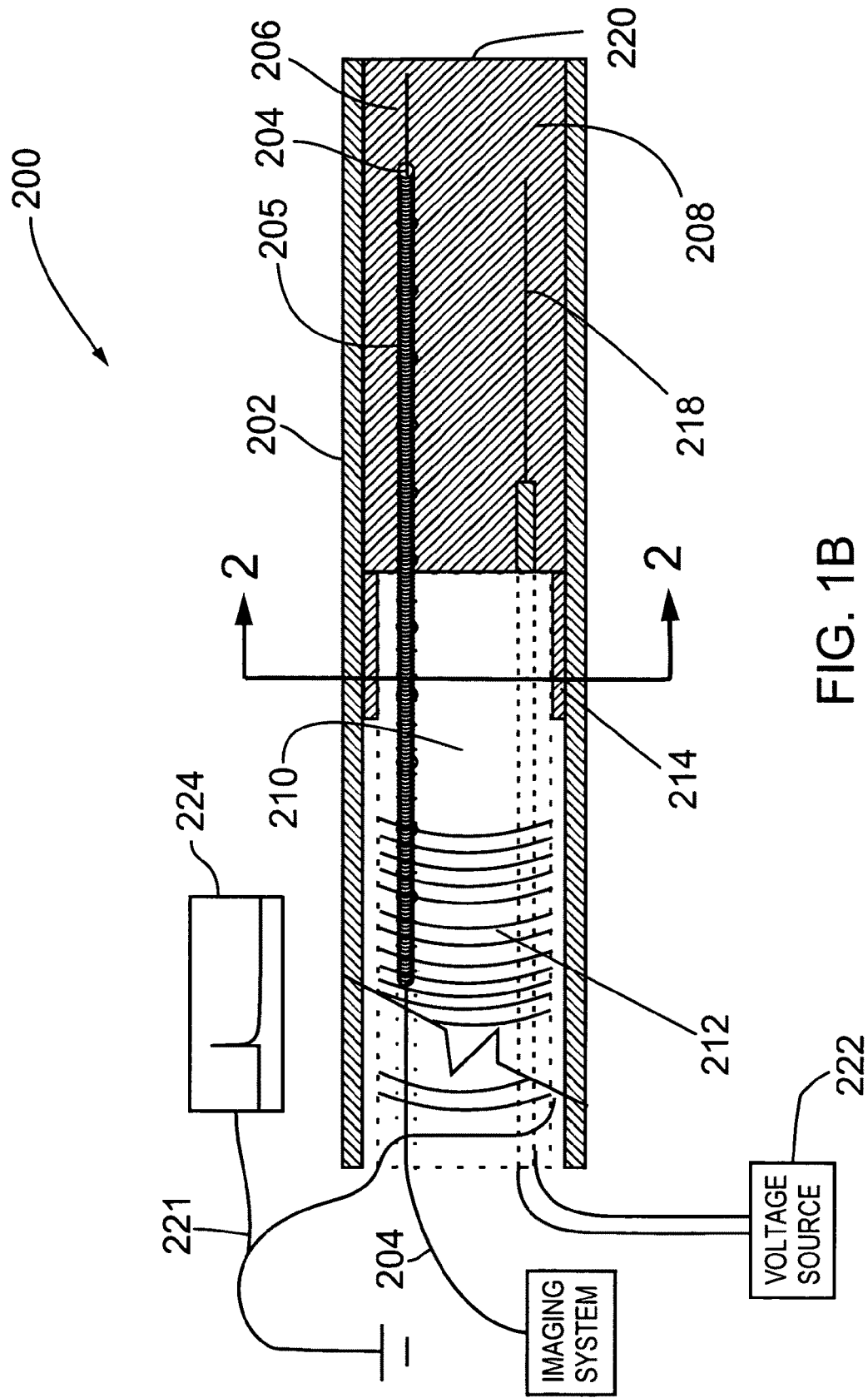
FIG. 1B is a cross sectional view of an embodiment of a forward looking ultrasound or OCT imaging probe using an electrode and a dissipative polymer catheter.
Figure 2:
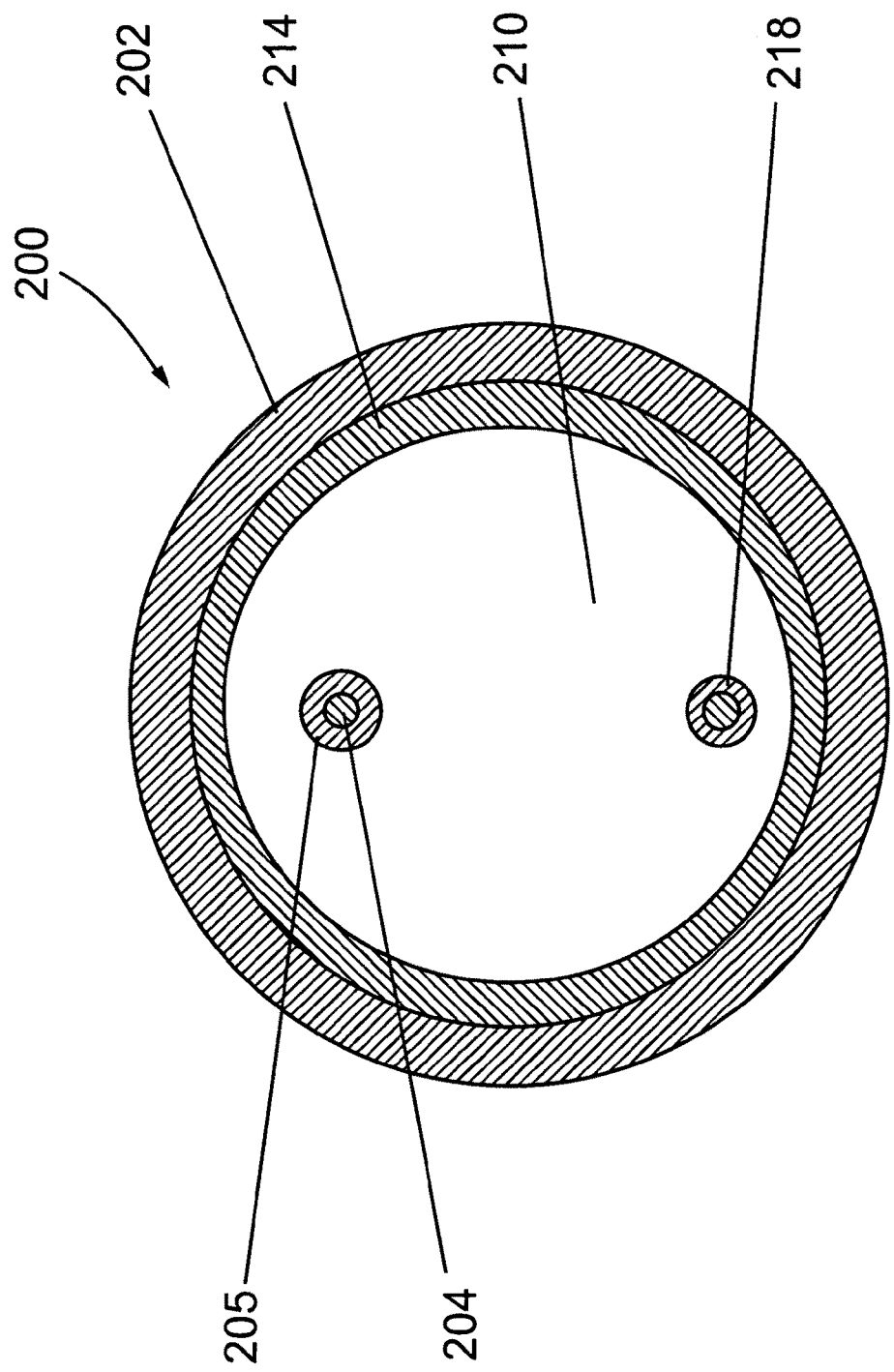
FIG. 2 is a cross sectional view of the probe of FIG. 1B taken along line 2-2.

FIG. 1B shows a cross sectional view of an embodiment of the front portion of probe 200 in a forward looking ultrasound or OCT imaging catheter probe using an electrode and a dissipative polymer catheter shown generally at 200. FIG. 2 is a cross sectional view of the probe of FIG. 1B taken along line 2-2 of FIG. 1B. Referring to FIGS. 1B and 2, probe 200 includes an outer sheath 202 which defines a distal front section which contains an imaging means, and a proximal back section. When the probe is configured for OCT, an imaging means 206 comprises an optical fiber (which forms the imaging conduit 204) which emits optical radiation from the front end of the optical fiber in the distal front section and the optical fiber is connected to a source of light through the proximal back section. This same optical fiber is capable of collecting the reflection of the emitted optical radiation from the tissue under examination and transfers this radiation to the optical circuits and electronics for detection. In the case where the probe is configured as an ultrasound probe the imaging means is an acoustic transducer located in the distal front section and the imaging conduit is an electrical wire connecting the transducer to a power supply through the proximal back section with a metal coil 205 disposed around the proximal end of the fiber/cable imaging conduit 204. The proximal back section of the probe 200 includes a volume 210 containing a dissipative polymer which is wrapped by a metal wire or coil 212.

The outer sheath 202 may be any plastic material of dimensions from about 300 to about 100,000 micrometers in diameter with wall thickness on the order of about 30 to about 1000 micrometers. Possible materials include, but are not limited to, PTFE (Teflon), polyethylene, nylon, polyetheretherketone (PEEK), nylon, acrylic (PMMA), polycarbonate (Lexan), polyimide, Latex, polyvinylchloride (PVC), silicone rubber, polyurethane and polyesters.

The distal front section of probe 200 includes a media 208. The media 208 in is transparent or semitransparent to the imaging ultrasound or optical energy. This media may be a gas, vacuum or fluid, such as for example air, as well as where in the media was air with a drop of water on the proximal end of the GRIN lens, and also with low density oils such as olive oil and mineral oil. Additional possibilities include the use of carbon dioxide or helium gas within the catheter sheath which is advantageous due to their high solubility in blood. The media, in the case of fluids, may serve to dampen the oscillatory motion of the cantilever such that slower scanning speeds may be obtained. Potential fluids for use as the media include, but are not limited to, olive oil, mineral oil, silicone oil (of viscosity between about 0.1 to about 400 centipoises) also possible are glycerol, ethanol and distilled water.

An adapter ring 214 is located at the front end of the proximal back section containing dissipative polymer in volume 210 between the dissipative polymer and the outer sheath 202 and a high voltage electrode 218 is located beside the section of the imaging conduit 204 wrapped in the coil 205 in the distal front section of probe 200. The purpose of the adapter ring 214 is to contain the media 208 located in the proximal compartment of the imaging probe. A high voltage power supply 222 is connected to the electrode 218. A circuit 221 parallel to the grounded metal wire or coil 212 forms a trigger signal monitor 224. This circuit 221 may possess a resistor to limit the current delivered to the trigger signal monitor 224. This trigger signal monitor 224 may be connected to an oscilloscope or a data acquisition system for image segmentation. This circuit provides a peak for each time that the cantilever (combined imaging conduit 204, coil 205 and fiber 204) touches the electrode 218 to be discussed hereinafter with the voltage being measured by the oscilloscope or the data acquisition card.

The functional purpose of the dissipative polymer in volume 210 of the catheter probe 200 is to allow an indirect electrical connection between ground potential and the cantilever (formed by combined coil 205 and the portion of the optical fiber 204 and/or ultrasound transducer located in the distal front section of probe 200). The dissipative polymer in volume 210 provides a finite migration time for the electrical charge to travel from the cantilever 204/205/206 to ground potential. It is this finite migration time that is used advantageously to provide an oscillatory motion and as well to limit electrostatic discharge within the catheter.

Generally, the dissipative polymer is made by either blending an antistatic agent (molecule) with another polymer or it may be made by adding conductive particles to a substantially insulating polymer.

A non-limiting example of a dissipative polymer that may be used in volume 210 is Pebax (trade name of Arkema group's polyether block amide (PEBA) compounds). This compound is also referred to as polyamide/polyether block copolymer. This polymer is a hydrophilic static dissipative polymer and a permanent antistatic polymer that is thermally stable. Its dissipative properties are independent of humidity. This polymer may be blended at 5% to 30% levels with Acrylonitrile butadience styrene (ABS), polycarbonate (PC), ABS/PC, polystyrene (PS), high impact polystyrene (HIPS), polybutylene terephtalate (PBT), acetal, polyvinyl chloride (PVC), polyethylene terephthalate (PET), polyethylene terephtalate glycol (PETG), or polyolefins.

Dissipative polymers may also be produced using other antistatic molecules combined with insulating polymers. Examples of additional antistatic agents include: PEDOT: PSS or Poly(3,4-ethylenedioxythiophene) poly(styrenesulfonate), Glyceryl monostearate, Octadecylbis(2-hydroxyethyl)amine, N,N-Bis(2-hydroxyethyl)dodecanamide, Tallow bis(2-hydroxyethyl)amine, Sodium sec-alkanesulfonate, Cocobis(2-hydroxyethyl)amine, Alkyl(C14-C18) bis(2-hydroxyethyl)amine, Oleylbis(2-hydroxyethyl)amine, Ethoquad T/13-50 Acetate, Ciba® IRGASTAT® P. These antistatic agents may be blended with low density polyethylene (LDPE), high density polyethylene (HDPE), polymethyl methacrylate (PMMA), Polyethylene terephthalate (PET), SAN, polypropylene (PP), polystyrene (PS), polycarbonate (PC) acrylonitrile-butadiene-styrene terpolymer (ABS), styrene acrylonitrile copolymer (SAN) Teflon (PTFE), polyvinyl chloride (PVC), polyethylene terephthalate glycol (PETG) and Nylon (polyamide) to form polymer mixtures.

Alternatively, examples of conductive particles that may be potentially added to the above list of insulating polymers include: carbon black, carbon fiber, indium tin oxide (ITO), indium tin oxide doped with an additional metal such as antimony. Stainless steel, copper, gold, silver, tin, and lead may also be added to the above list of polymers in either particulate or fiber form to create a static dissipative effect.

The metallic coil 205 around the fiber/cable 204 forming the imaging conduit provides the function of metallizing the imaging conduit 204 as well as shielding the conduit itself from high voltage field. The metallic coil 205 may be a platinum coil of 300 micrometers in diameter. The coil 205 may be of dimensions between about 50 to about 1000 micrometers in diameter. The coil 205 may be comprised of any conductive metal such as, but not limited to, platinum, gold, copper, silver, steel, lead, aluminum and any of their alloys. The metallic coil 205 may also be replaced by a metal coating on the imaging conduit where the metal is comprised of, but not limited to, gold, chrome, brass, copper, or platinum.

The metal wire or coil 212 wrapped around the dissipative polymer in volume 210 provides a connection to ground potential through circuit 221. Wire 212 may be any conductive metallic wire such as, but not limited to, copper, gold, lead, steel, platinum or any of their alloys. Wire 212 may also be fashioned in counter woven strands as described by Crowley et al. (U.S. Pat. No. 5,372,138) such that it would enable a torque applied at the proximal end of the catheter to be transmitted to the end. This cable would, therefore allow an angular rotation produced at one end to be transmitted to the other. Combining this rotation with the scanning of the cantilever would allow the cantilever to scan the two dimensional plane in front of it. Employing optical coherence tomography or ultrasound imaging with this complete two dimensional scan would allow for a three dimensional imaging volume to be obtained.

The electrode 218 shown in FIG. 1B may be an insulated wire and may be a copper beryllium alloy wire that includes four insulating layers. Additional possibilities include wires of dimensions from about 50 to about 1000 micrometers in diameter comprised of, but not limited to, steel, copper, gold, platinum, silver, iron or any of their alloys. The wire forming electrode 218 may or may not possess a single or a plurality of insulating layers.

A seal 220 for the probe located at the most distal end of the distal front section of the probe 200 would be required for use inside in a living organism. This seal 220 acts to seal the media 208 so that it remains within the front section of the probe 200 without being contaminated by fluid from the imaging field inside the patients body being imaged with the probe. The seal 220 would be anywhere from about 10 to about 4000 micrometers thick depending on the intending imaging field of the probe 200. This seal 220 is preferably made of a material that is transparent to either optical and/or acoustic energy. Potential materials include a wide range of plastics such as but not limited to PTFE (Teflon), polyethylene terephthalate (PET), nylon, polyetheretherketone (PEEK), nylon, Poly(methyl methacrylate) (PMMA), polycarbonate (Lexan), polyimide, Latex, polyvinylchloride (PVC), silicone rubber, polyurethane and polyesters. A glass window may also be possible in some embodiments as may the use of a precisely fitted GRIN lens. Liquid sealants may also be employed in conjunction with the materials described above.

Figure 8:
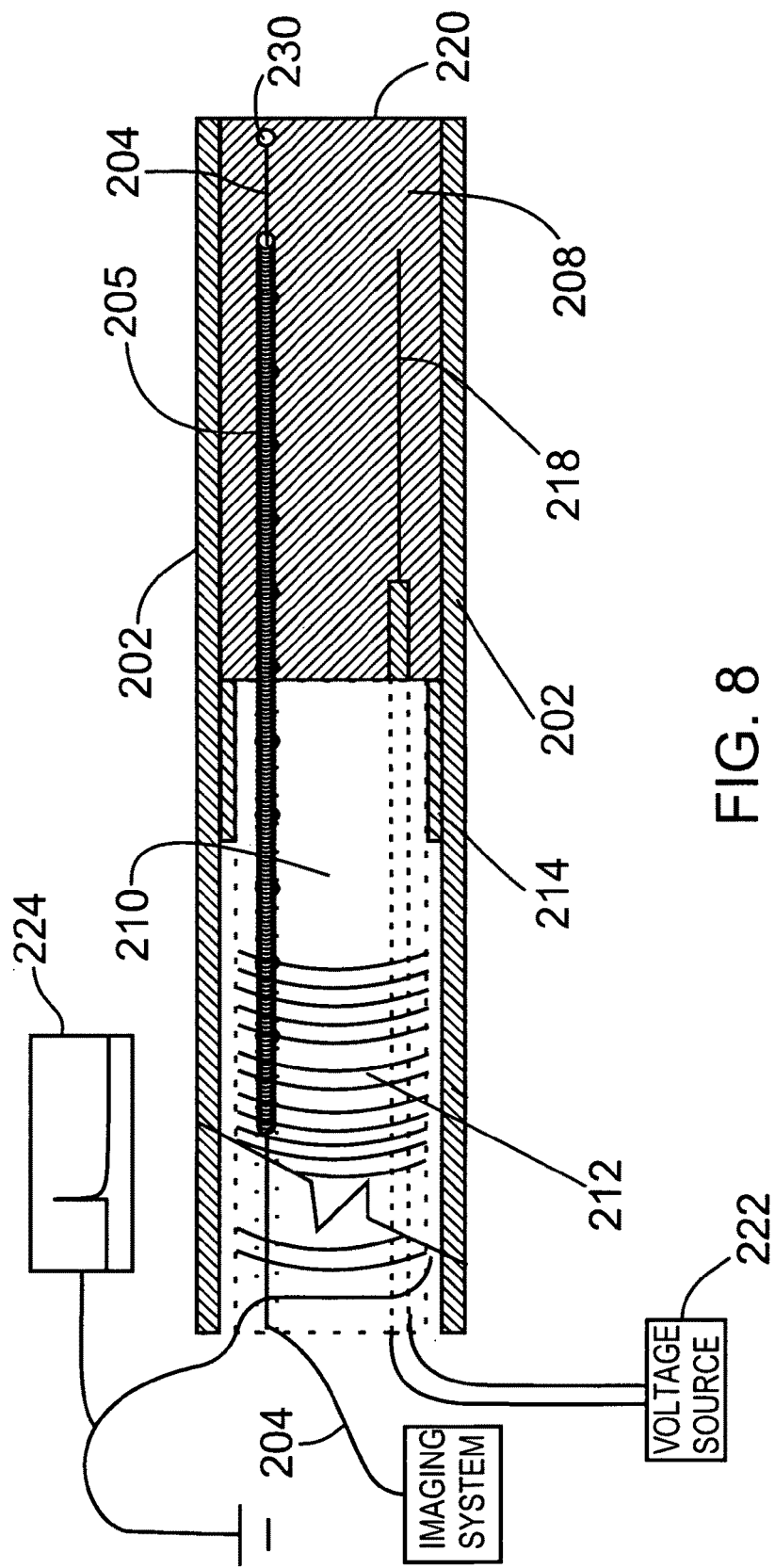
FIG. 8 is a cross sectional view of another embodiment of an imaging probe configured for use as an optical probe in which the focusing element is a ball lens on the optical fiber.
Figure 9:
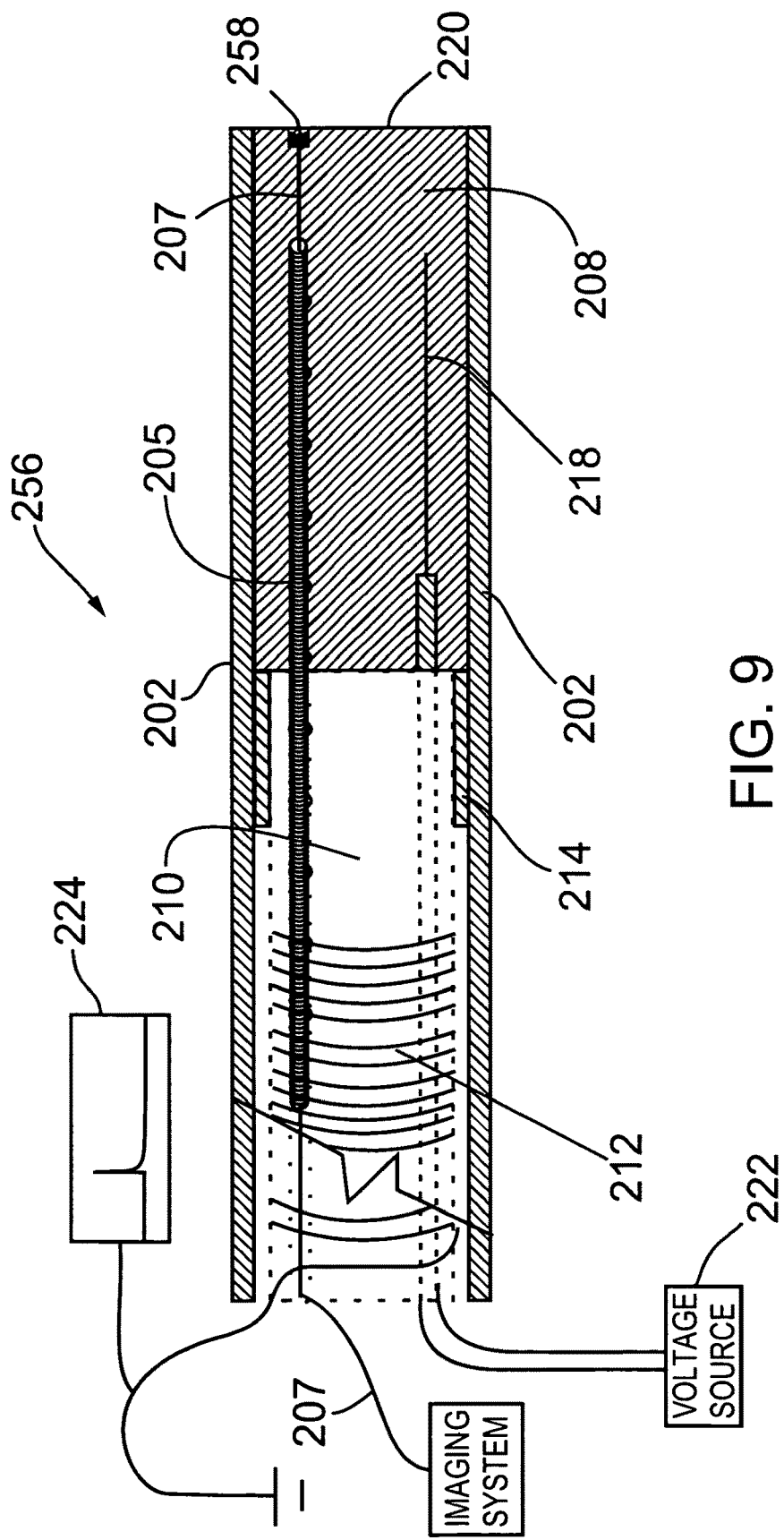
FIG. 9 is a cross sectional view of another embodiment of an imaging probe configured for use as an ultrasound probe having an ultrasound transducer mounted on the end of a microcoaxial cable.

The imaging conduit 205 may be either an optical fiber for optical imaging, or a micro coaxial cable with an ultrasound transducer affixed to its end for ultrasound imaging. More particularly, imaging conduit 205 may either be a fiber optic cable capable of transmitting and receiving optical energy of wavelengths between about 250 to about 2000 nm. The fiber optic may be between about 15 to about 400 micrometers in diameter. The probe 240 shown in FIG. 7 has a fiber optic forming the imaging conduit 204 to which there is coupled to a GRIN lens 228, while FIG. 8 shows a probe 250 having a ball lens 230 fused to the distal end of fiber optic 204. FIG. 9 shows a probe 256 configured with an ultrasound transducer 258 affixed to the distal end of a micro coaxial cable 207 for ultrasound imaging. The microcoaxial cable 207 may be between about 50 to about 400 microns in diameter.

The catheter used for initial experiments was a three lumen catheter to allow for separate lumens for the cantilever and two electrodes—a ground and a high voltage electrode. Also claimed are applications in which the dissipative polymer catheter possesses only a single lumen or multiple lumens such as 2-10 separate lumens within the dissipative polymer.

Figure 3:
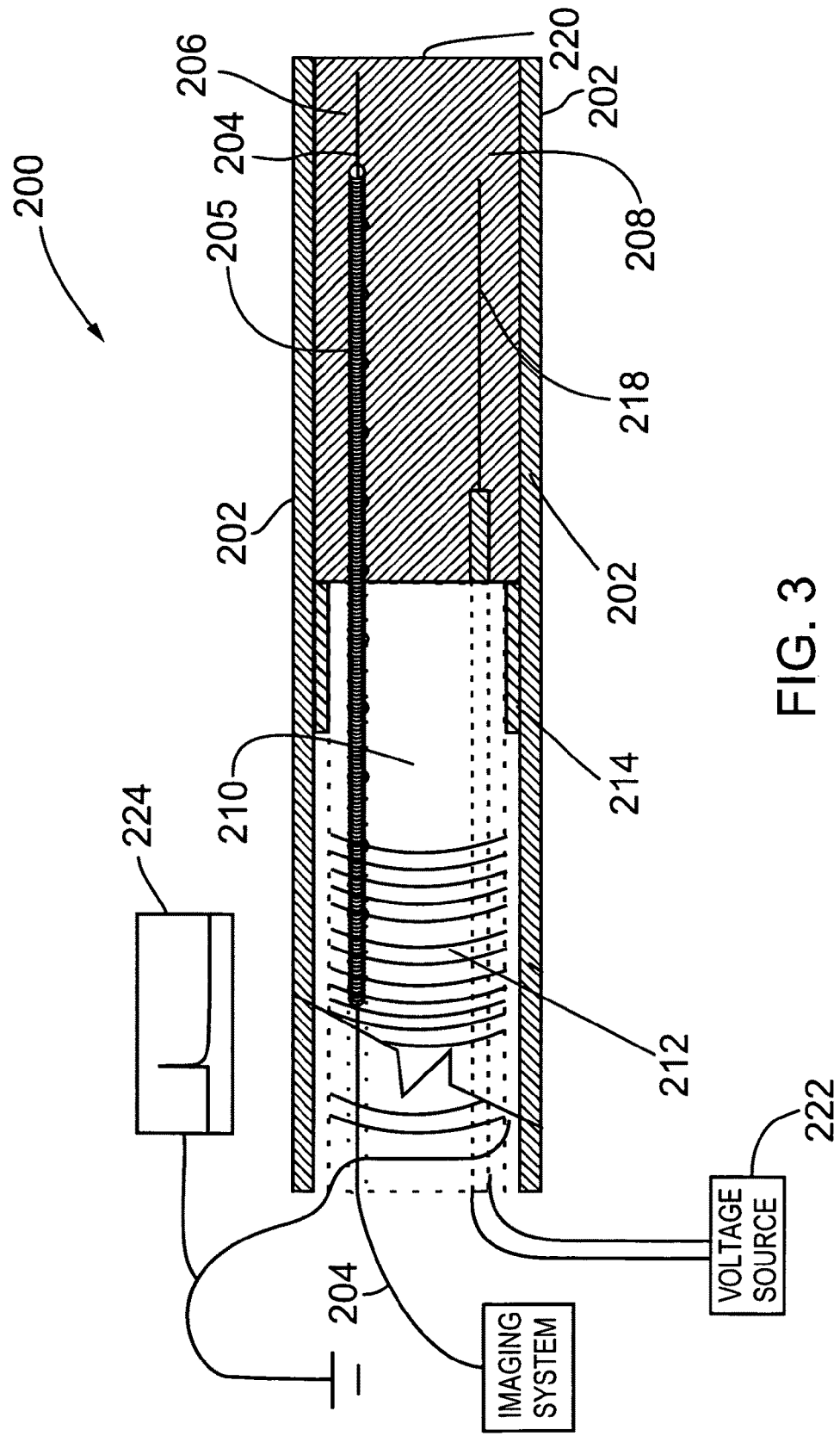
FIGS. 3 to 6 are cross sectional views similar to FIG. 1B illustrating a time sequence during operation in which an optical or acoustic signal emitter is displaced.
Figure 4:
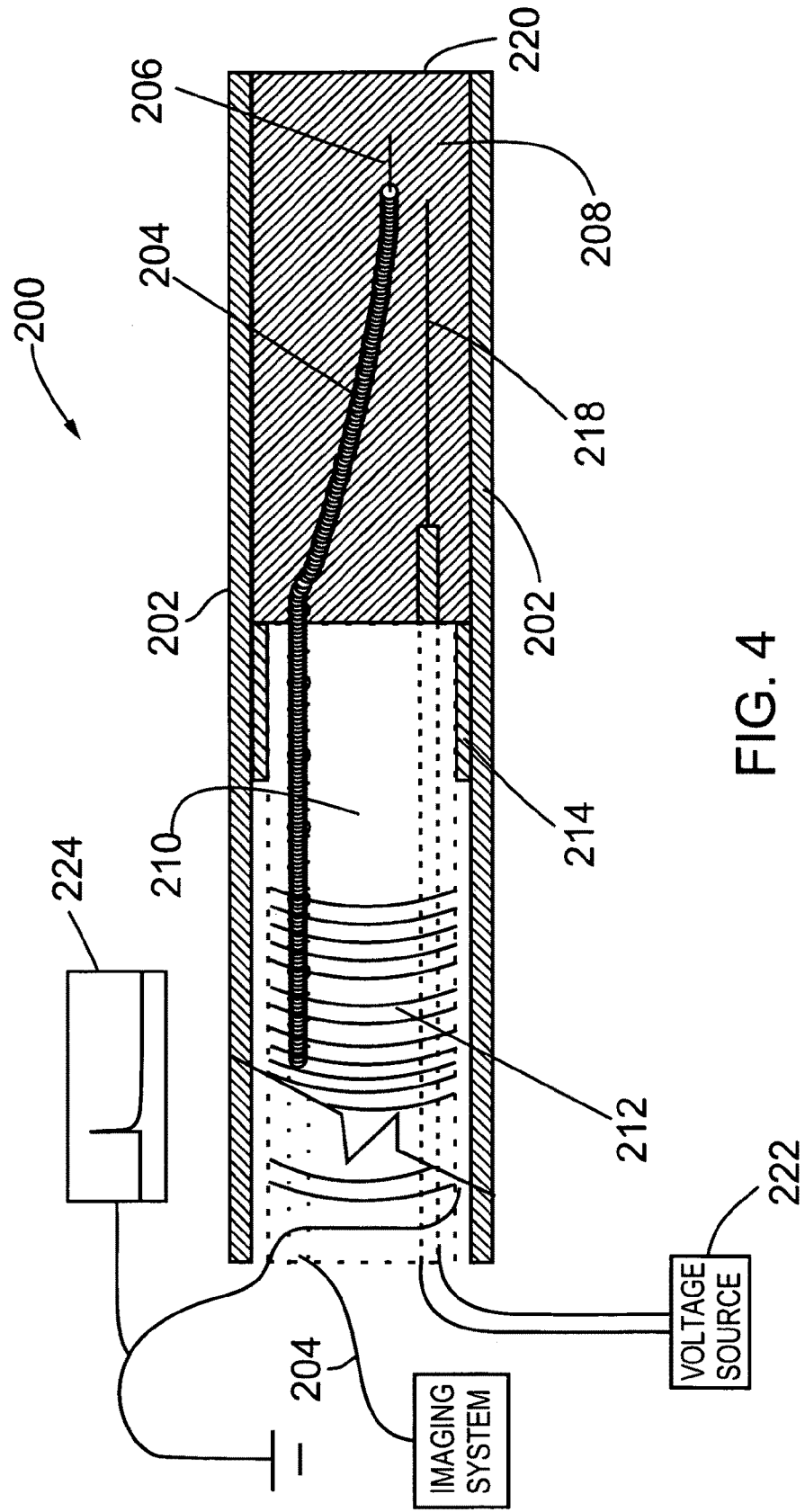
Figure 5:
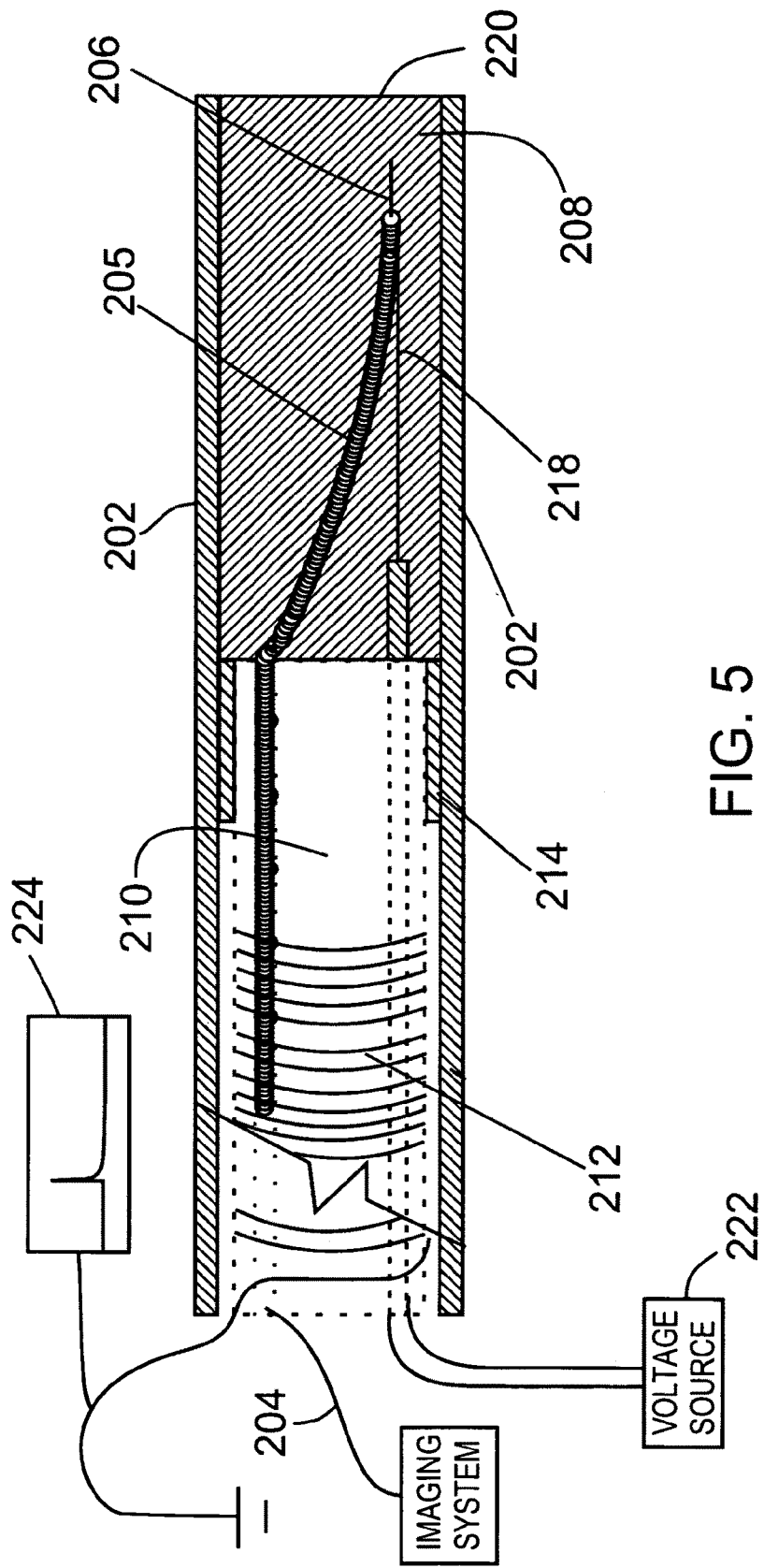
Figure 6:
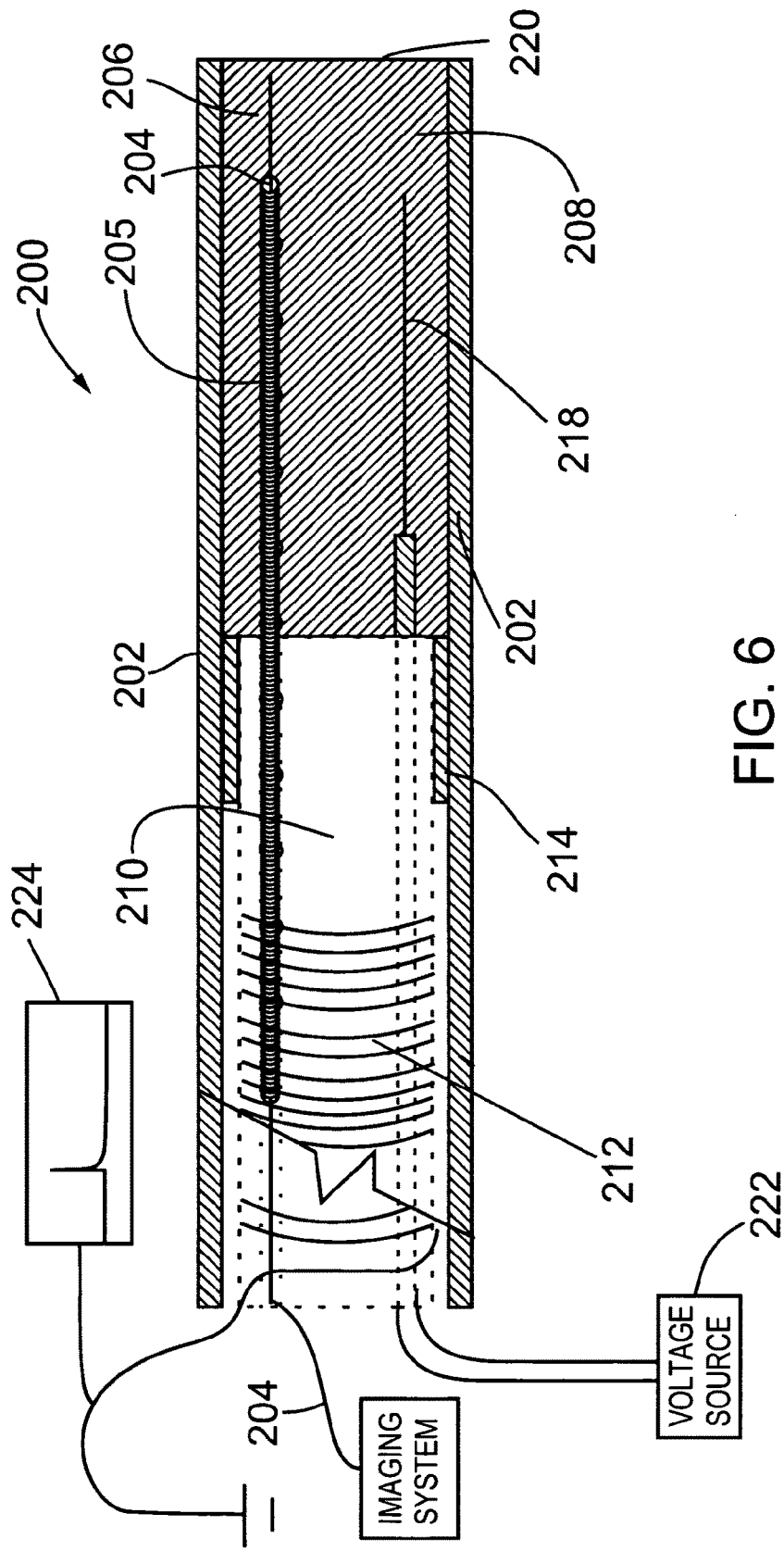
Figure 7:
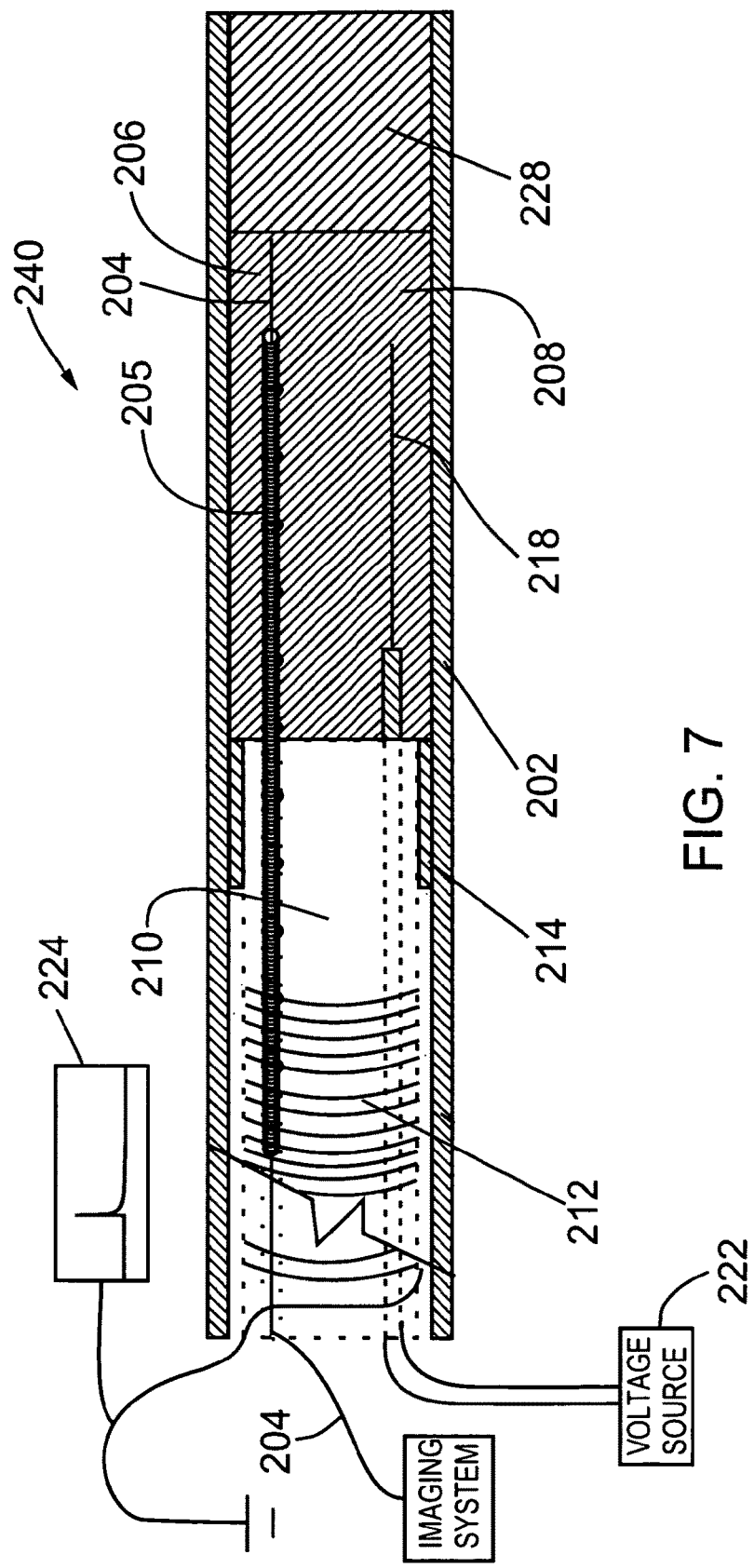
FIG. 7 is a cross sectional view of another embodiment of an imaging probe configured for use as an optical probe in which the focusing element includes a GRIN lens.

FIGS. 3 to 6 illustrate a time sequence during operation of probe 200 in which an optical or acoustic signal emitter is displaced. FIG. 3 shows the probe immediately after the potential has been applied; the cantilever at this point is electrically neutral and therefore is attracted to the electrode. FIG. 4 shows the cantilever undergoing some deflection towards the electrode 218. FIG. 5 shows the cantilever in contact with the electrode 218, this results in the coil 205 acquiring a similar charge from the electrode 218. This charge causes the coil 205 and hence fiber 204 to be repelled from the electrode 218 as like charges repel. This acquisition of charge is observed in the parallel circuit 221 as shown in the Figures as a spike on the trace in circuit 224. Thus the coil 205 and hence fiber 204 (and/or ultrasound transducer) returns to its original position allowing the cycle to begin again as shown in FIG. 6.

Figure 10:
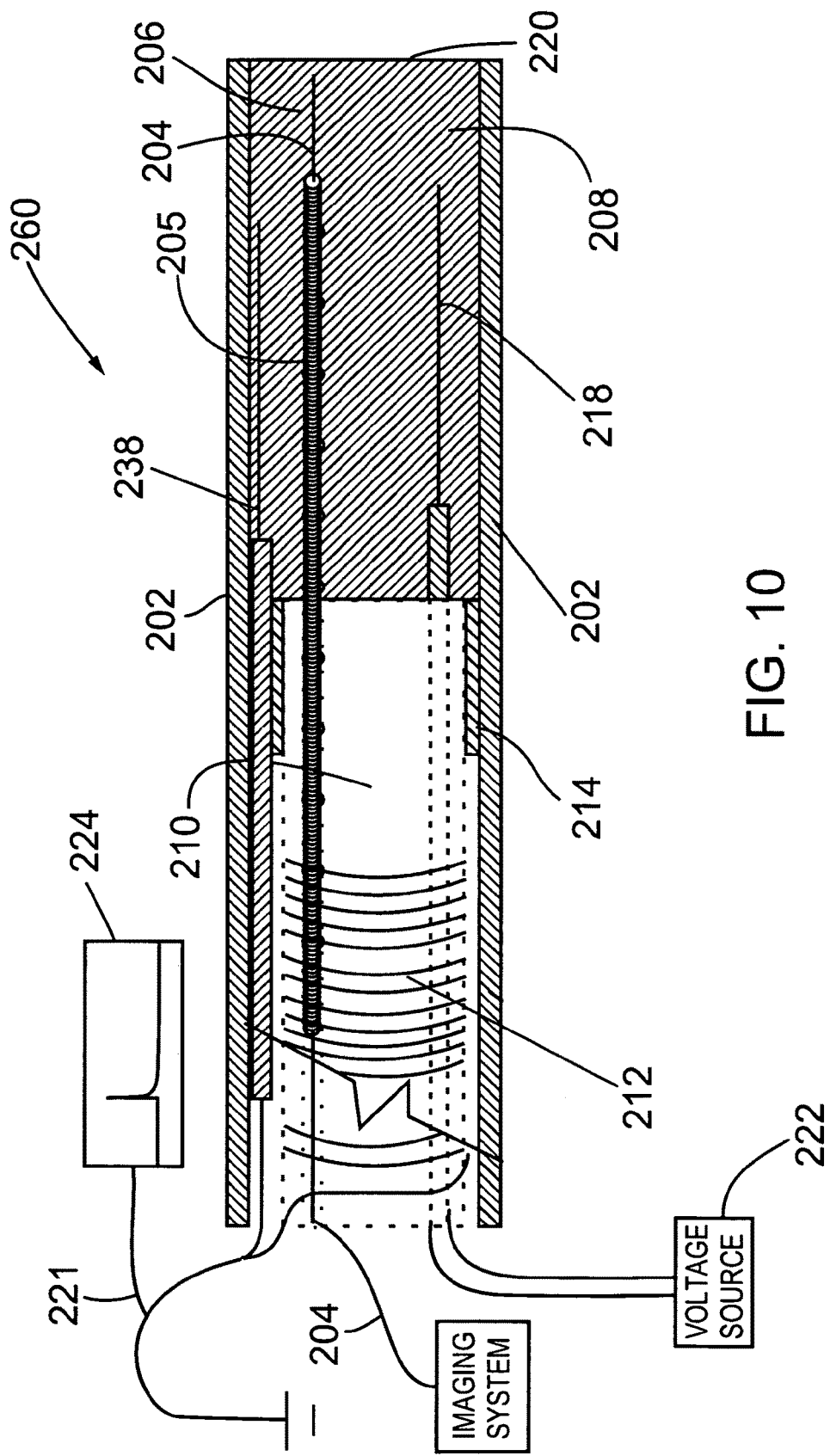
FIG. 10 is a cross sectional view of another embodiment of an imaging probe in which two wires are used with one wire connected to the inside of the sheath and grounded and the second wire acts as an electrode.
Figure 11:
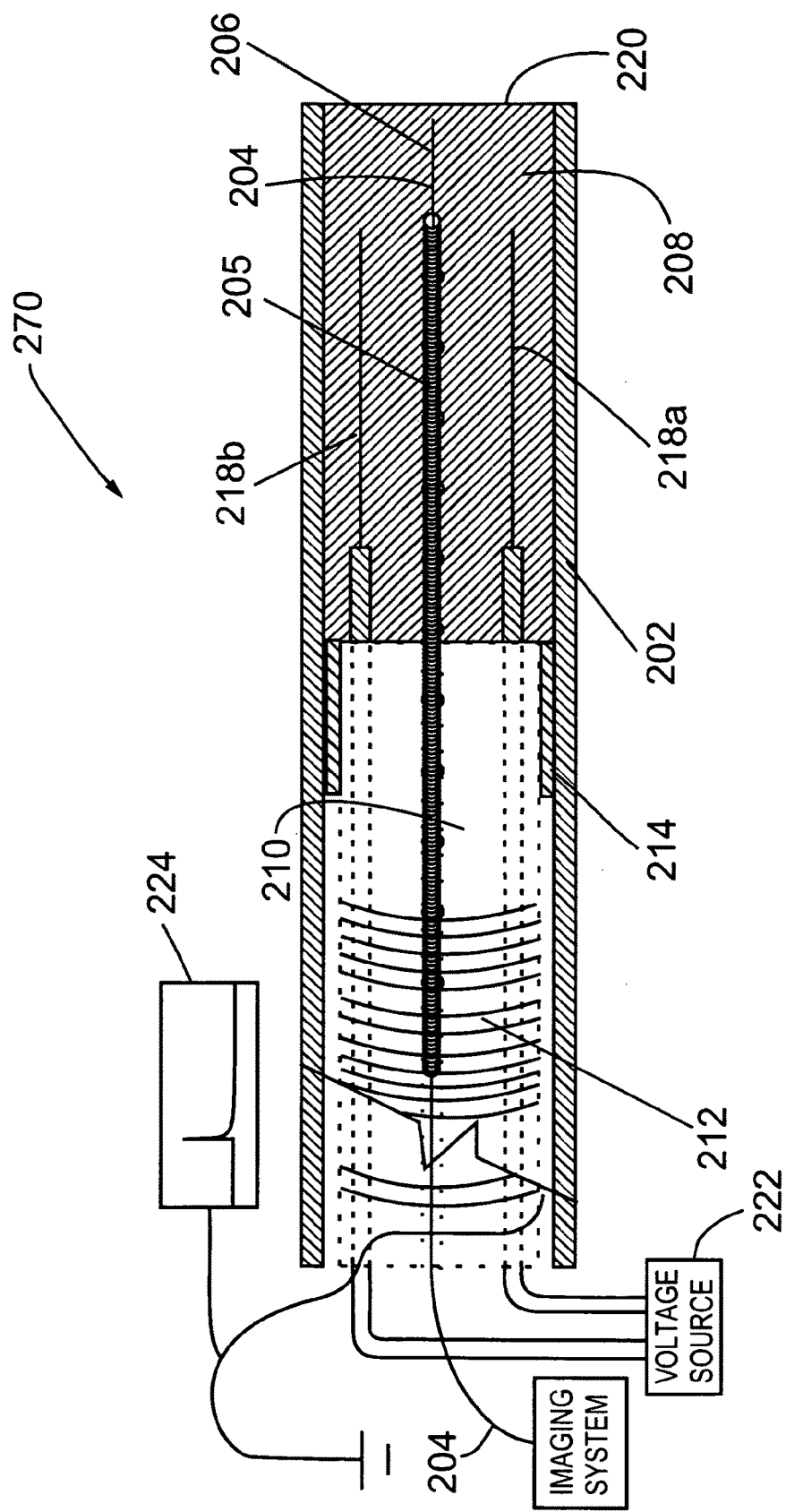
FIG. 11 is a is a cross sectional view of another embodiment of an imaging probe in which two wires are used and each wire may be connected to a time varying voltage source or each wire may be alternatively activated and deactivated.
Figure 12:
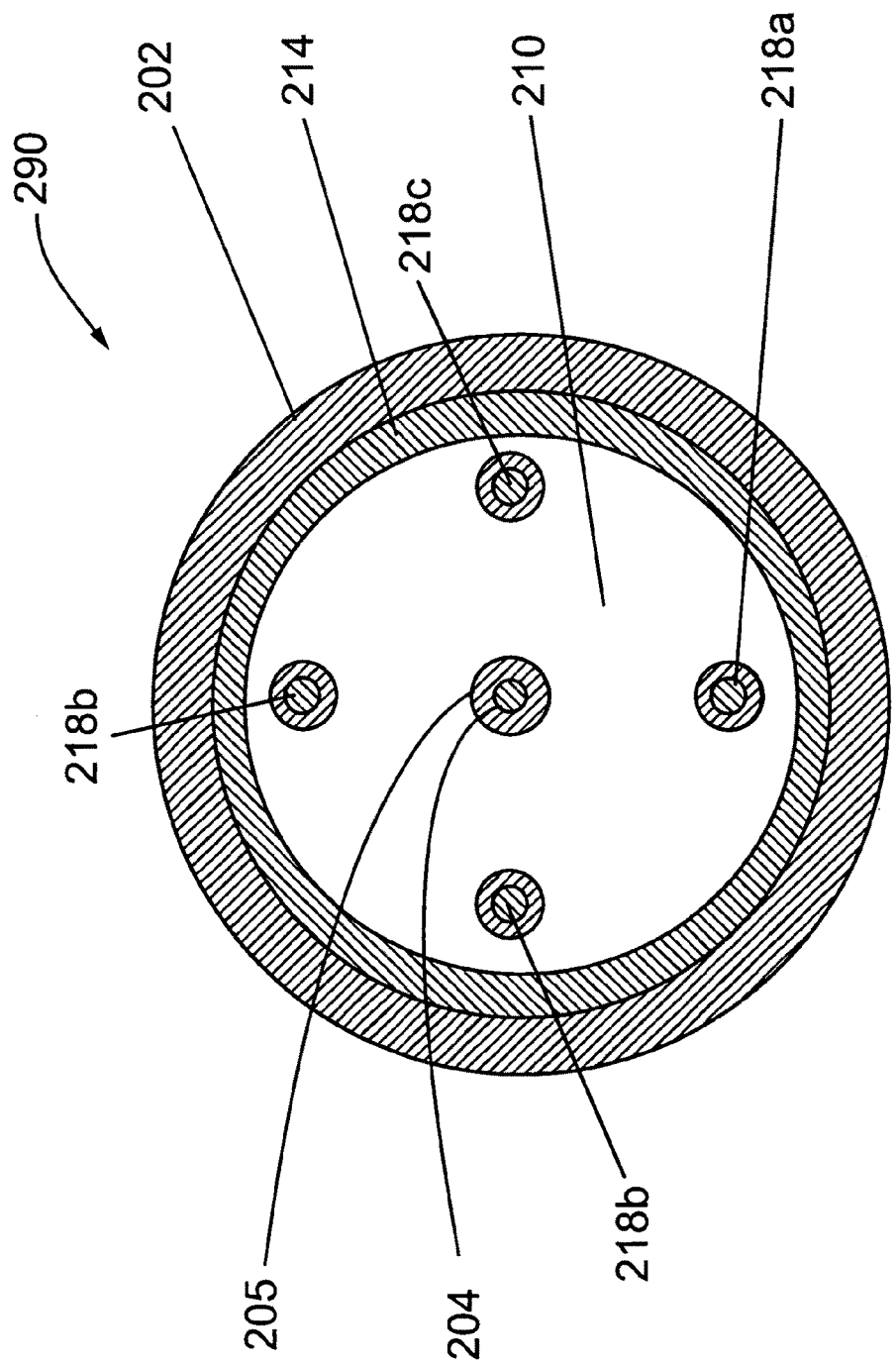
FIG. 12 is a sectional view through the diameter of an alternative embodiment of an imaging probe in which four wires arranged at ninety degrees to each other are used to actuate the cantilever.

FIGS. 10, 11 and 12 illustrate different embodiments of the catheter probe whereupon two wires are used in the imaging component.

In probe 260 shown in FIG. 10 electrode 218 is connected to the high voltage source 222 as in FIG. 1B, while the other wire 238 is connected to ground potential through ground circuit 221 and therefore acts as a ground electrode. This ground wire (ground electrode) 238 allows the cantilever to quickly dissipate all of its acquired charge upon contact and immediately be attracted to the high voltage electrode 218 once again. Thus, this ground wire 238 allows for more rapid oscillation than was observed in embodiments without this ground wire 238 that the coil 205 could take several seconds after repelling from the electrode 218 before it was once again attracted. When the ground wire 238 was added, this delay was eliminated. The presence of this ground wire 238 in close vicinity to the electrode 218 also insures that any electrostatic discharges will be delivered to the ground electrode 238 rather than the tissue under examination. In this probe 260 as before the imaging conduit 204 may be an optical fiber or a microcoaxial cable with a transducer.

In probe 270 shown in FIG. 11 two electrodes, 218a and 218b are both connected to the high voltage source 222. Time varying electrical potentials may be applied independently to either electrode 218a and 218b to allow for a desired scanning motion of the cantilever. Coupling to ground is provided by the wire 212 wrapped around the dissipative polymer in the proximal back section of probe 270. In addition, or alternatively, in this embodiment either one of the electrodes 218a and 218b, may be grounded at one time.

FIG. 12 shows a cross section of an embodiment of a catheter imaging probe 290 using four (4) electrodes 218a, 218b, 218c and 218d arranged as illustrated in order to provide actuation of the cantilever. In this embodiment, the four wires may possess different individual electrical potentials. In this embodiment each of the electrodes 218a to 218d may be driven individually at different voltages in order to adjust the angle by which the metallic coil and the imaging conduit move thereby to provide two dimensional control of the cantilever. Used in conjunction with an imaging conduit containing an ultrasound, or an optical coherence tomography probe, this embodiment may be used to form three dimensional images.

Figure 13:
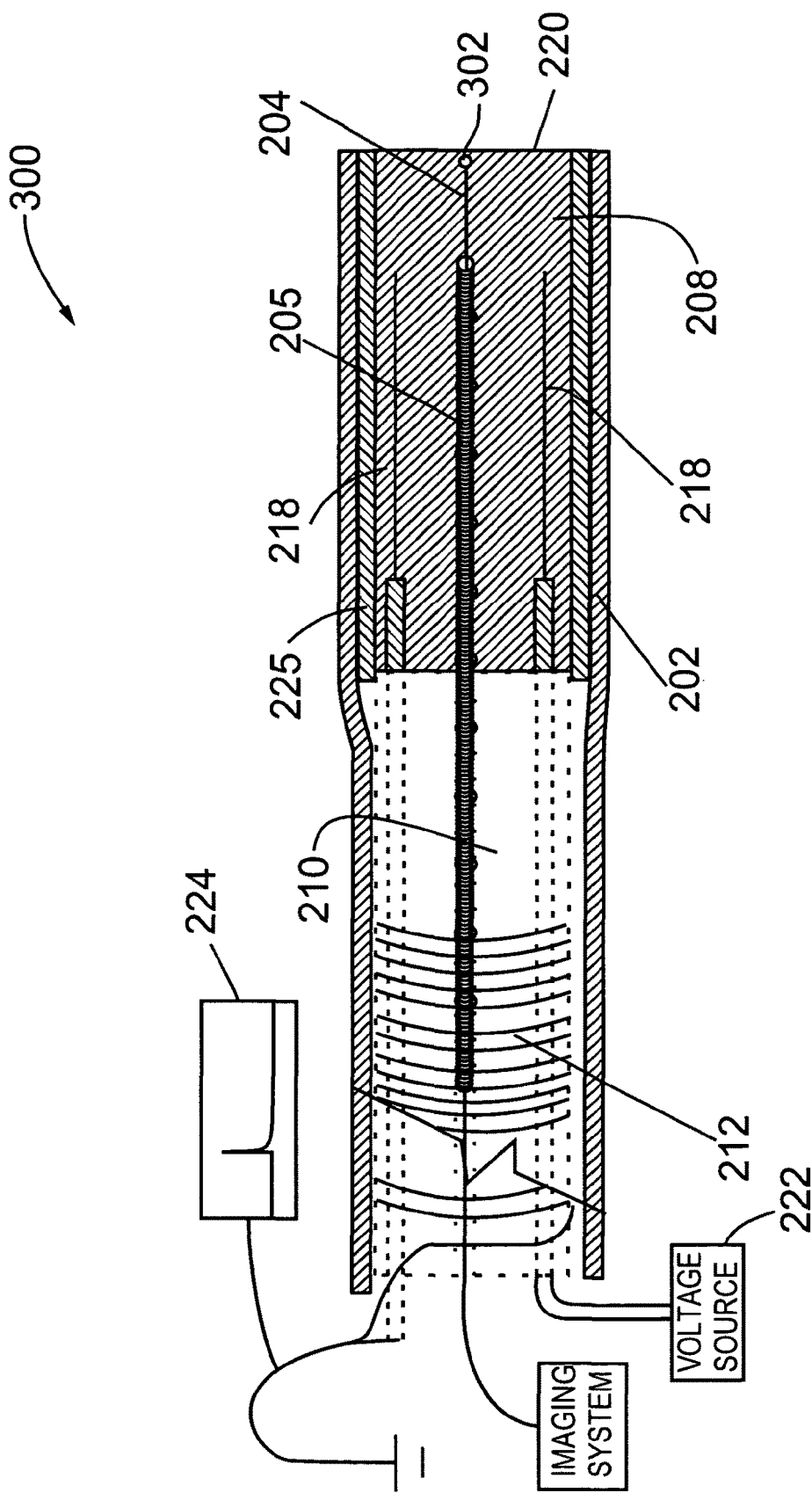
FIG. 13 is a cross sectional view of another embodiment of an imaging probe in which a three lumen dissipative polymer catheter is used in conjunction with a fiber optic with an affixed ball lens.

FIG. 13 shows a three lumen embodiment of a catheter probe 300 in which the distal front section of the outer sheath 202 is flared out to accommodate a rigid tube 225. This rigid tube 225 is used to facilitate alignment of the distal portion of the catheter. This rigid tube 225 may be composed of, but not limited to, polymide, polycarbonate, glass, nylon or urethane. This embodiment of the probe 300 shows the imaging conduit 204 as a fiber optic with a ball lens 302 attached to it. The ball lens 302 serves to focus the light a distance of 10 to 3000 microns in front of the lens 302. It will be appreciated by those skilled in the art that the ball lens 302 may be replaced with a multimode graded index fiber of a specified length such that the fiber length serves to focus the light a pre-selected distance in front of the distal end of the probe 300. Alternatively one could use a miniaturized axicon (conical) lens at the end of the fiber 206 to create a "Bessel beam" that would not diverge as it propagates.

Figure 14:
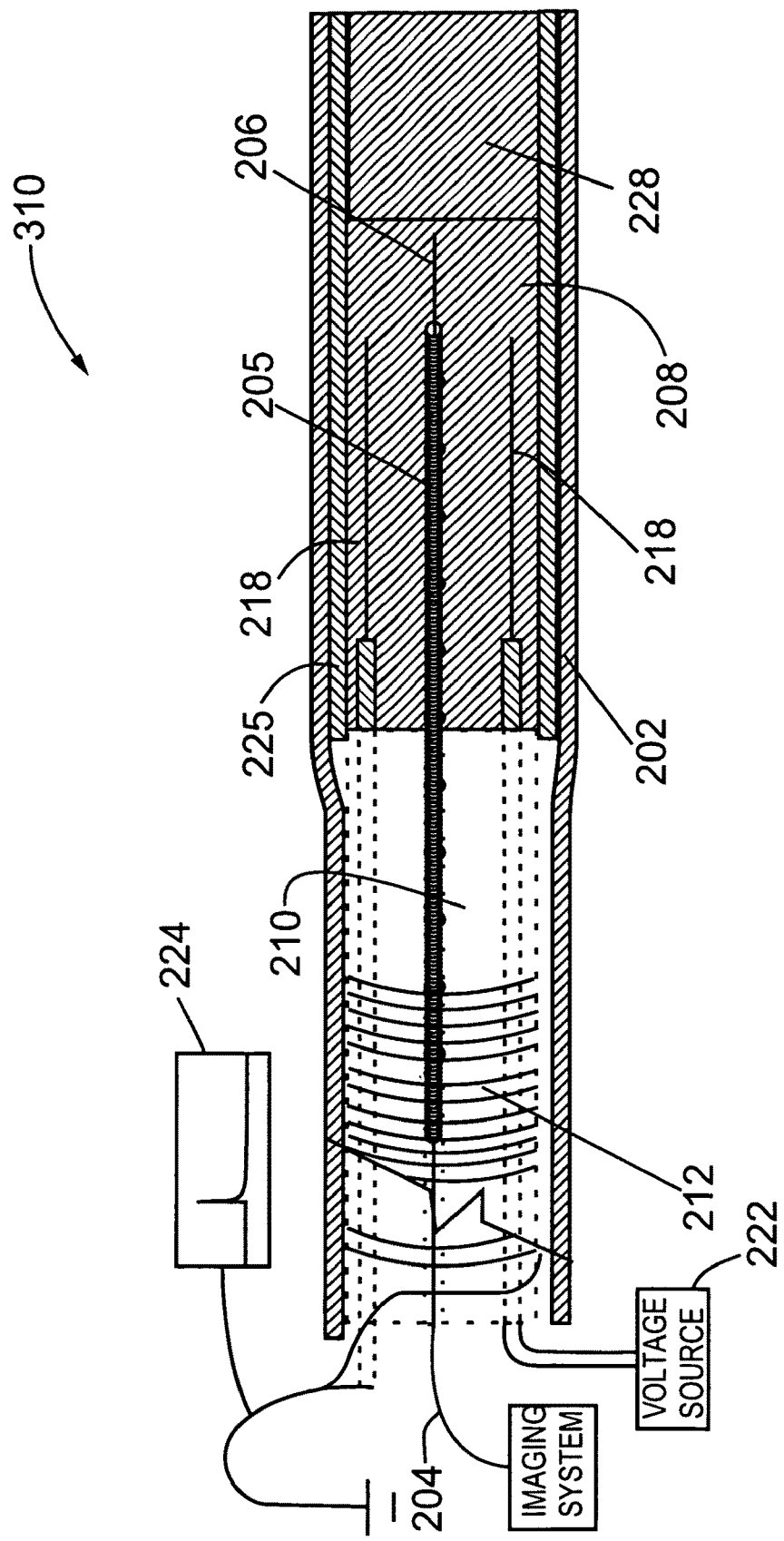
FIG. 14 is a cross sectional view of another embodiment of an imaging probe in which a three lumen catheter is combined with a fiber optic that is scanned proximally to a GRIN lens.

FIG. 14 shows another embodiment of a three lumen catheter probe 310 with the imaging conduit including a fiber optic 204 that is scanned proximal to GRIN lens 228. By scanning the fiber proximal to a GRIN lens 228 the lateral displacement of the fiber 204 is translated into both a lateral displacement of the exiting beam as well as an angular offset of the exiting beam. It will be understood that the GRIN lens 228 may be replaced with a ball-lens or "fish eye" style lens or combination of lenses. Also possible would be to replace the GRIN lens 228 with a circular array of micro lenses. In these examples the fiber optic 204 would be scanned proximal to the imaging optics.

Figure 15:
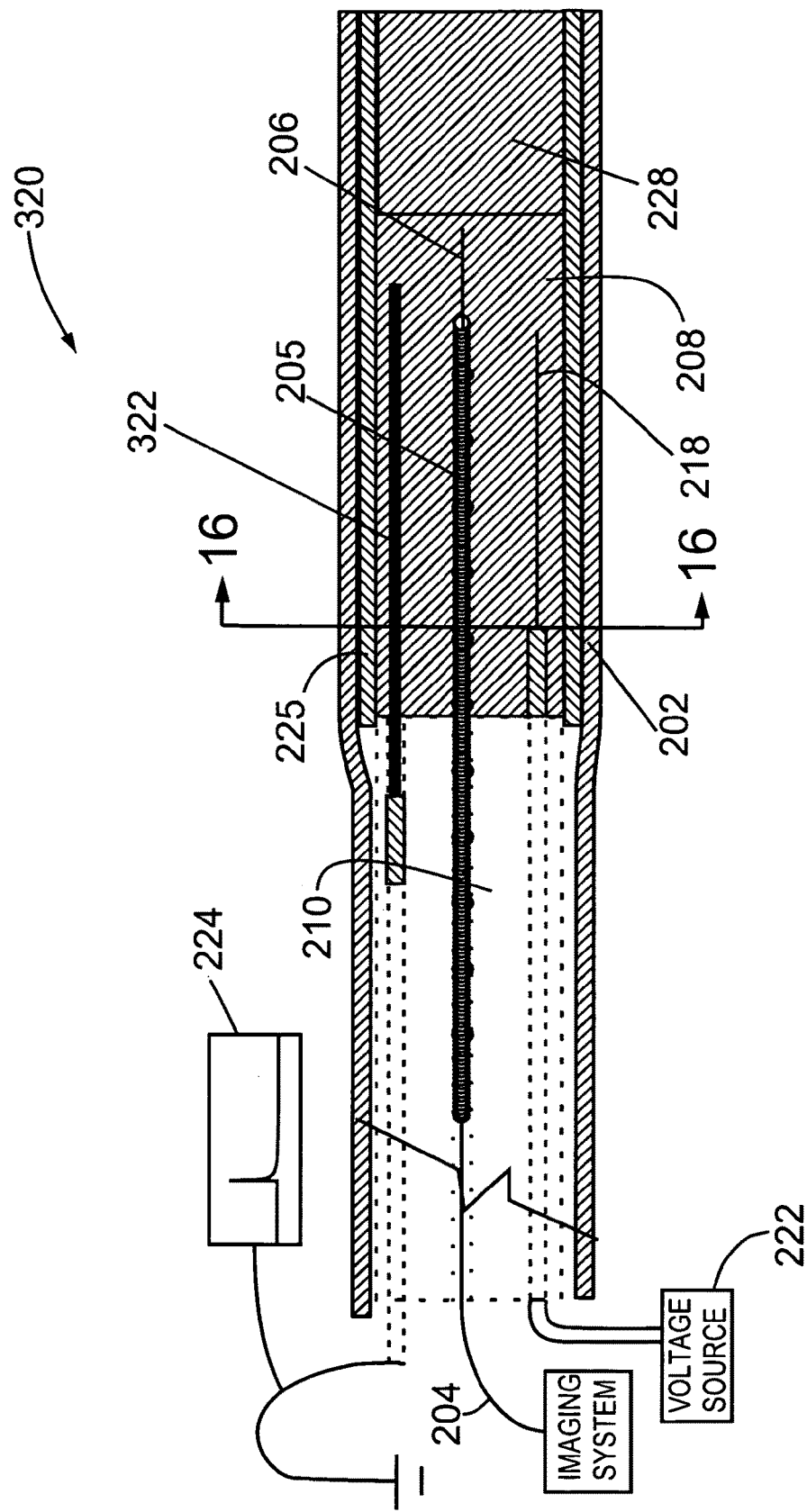
FIG. 15 shows a similar embodiment to FIG. 14 with the exception that the coupling to ground is instead provided by an exposed wire within one of the lumens.
Figure 16:
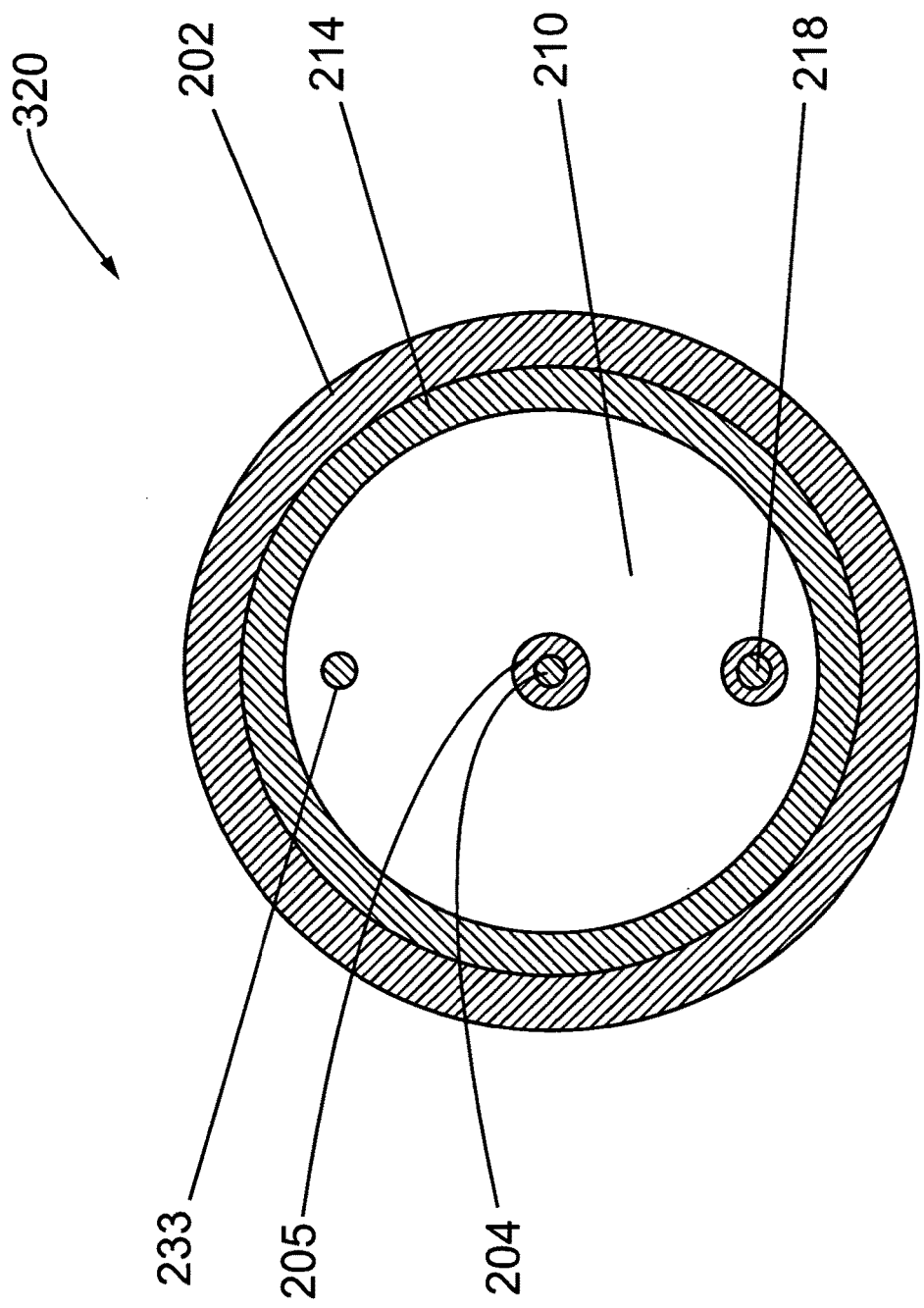
FIG. 16 is a cross-section view of the probe shown in FIG. 15 taken along the line 16-16.

FIG. 15 illustrates another three lumen embodiment of a probe 320 in which an exposed portion of grounded electrode 322 is located within the proximal back portion of probe 320 in volume 210 containing the electrically dissipative polymer such that the exposed conductive portion of the grounded electrode 322 is in contact with the dissipative polymer material. This portion of electrode 322 thus provides a coupling to ground for the charge. This electrode 322 may be used to replace, or be used in conjunction with, grounding materials on the outside of the dissipative polymer. By varying the amount of conductive surface of the ground electrode 322 touching the inside of the polymer, it is possible to increase or decrease the coupling strength of the cantilever to ground. An increased coupling to ground will result in a larger force of attraction towards the applied voltage. FIG. 16 shows a cross-section of FIG. 15 along the 16-16 line as shown.

Figure 17:
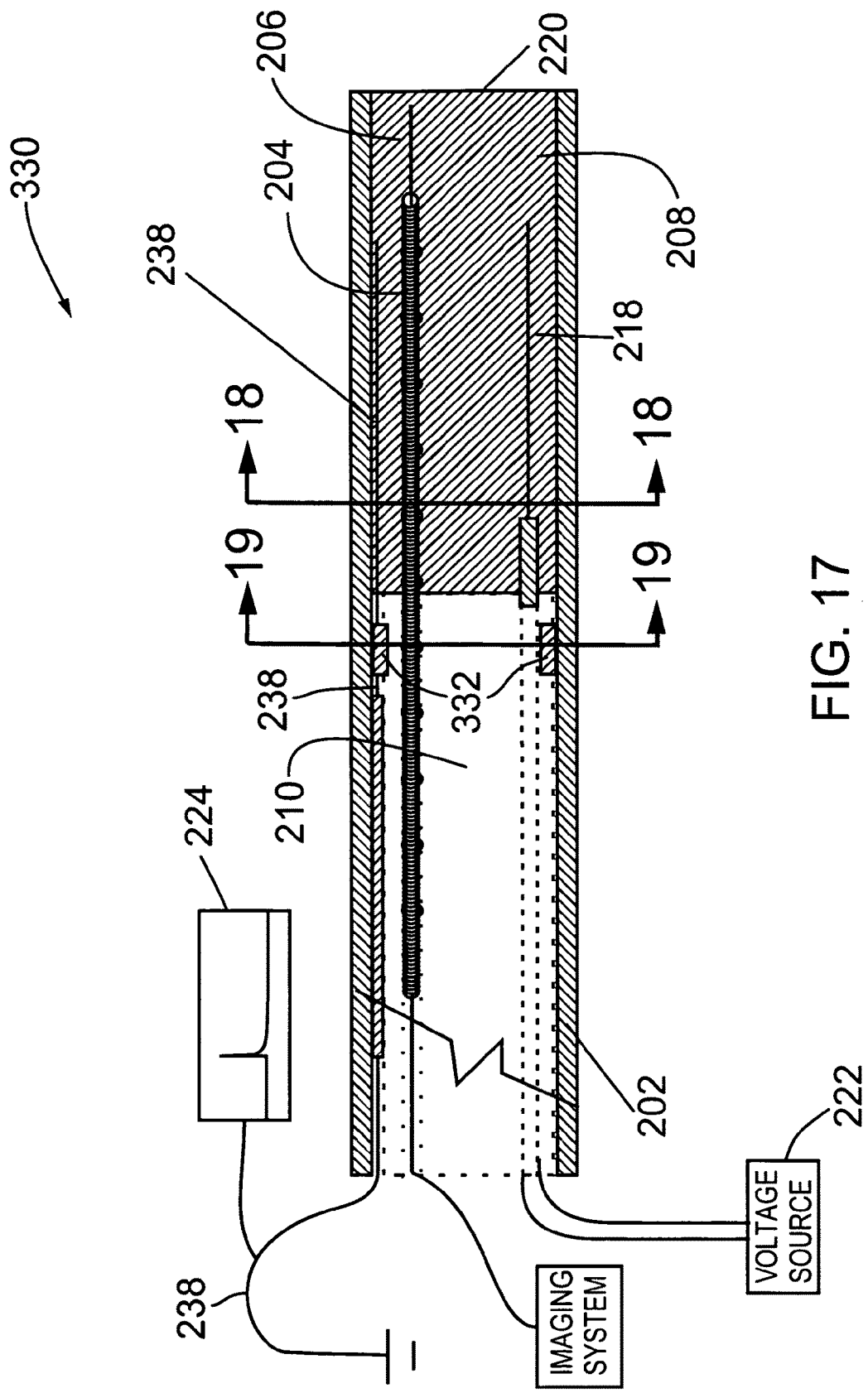
FIG. 17 is a cross sectional view of another embodiment of an imaging probe in which an electrode with a ring element is fitted over the dissipative polymer catheter to provide a ground.
Figure 18:
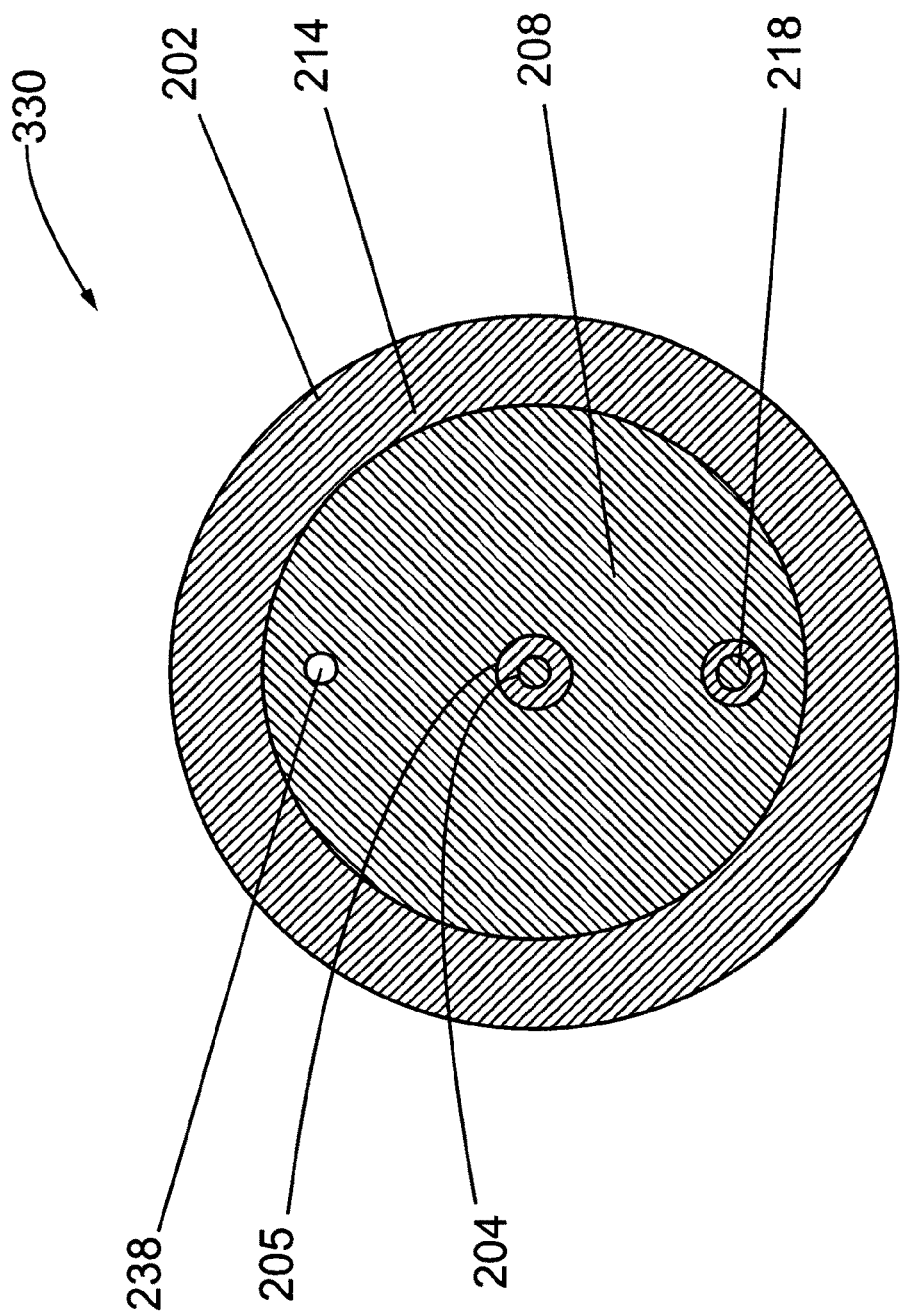
FIG. 18 is a cross section view of the probe shown in FIG. 17 along the line 18-18.
Figure 19:
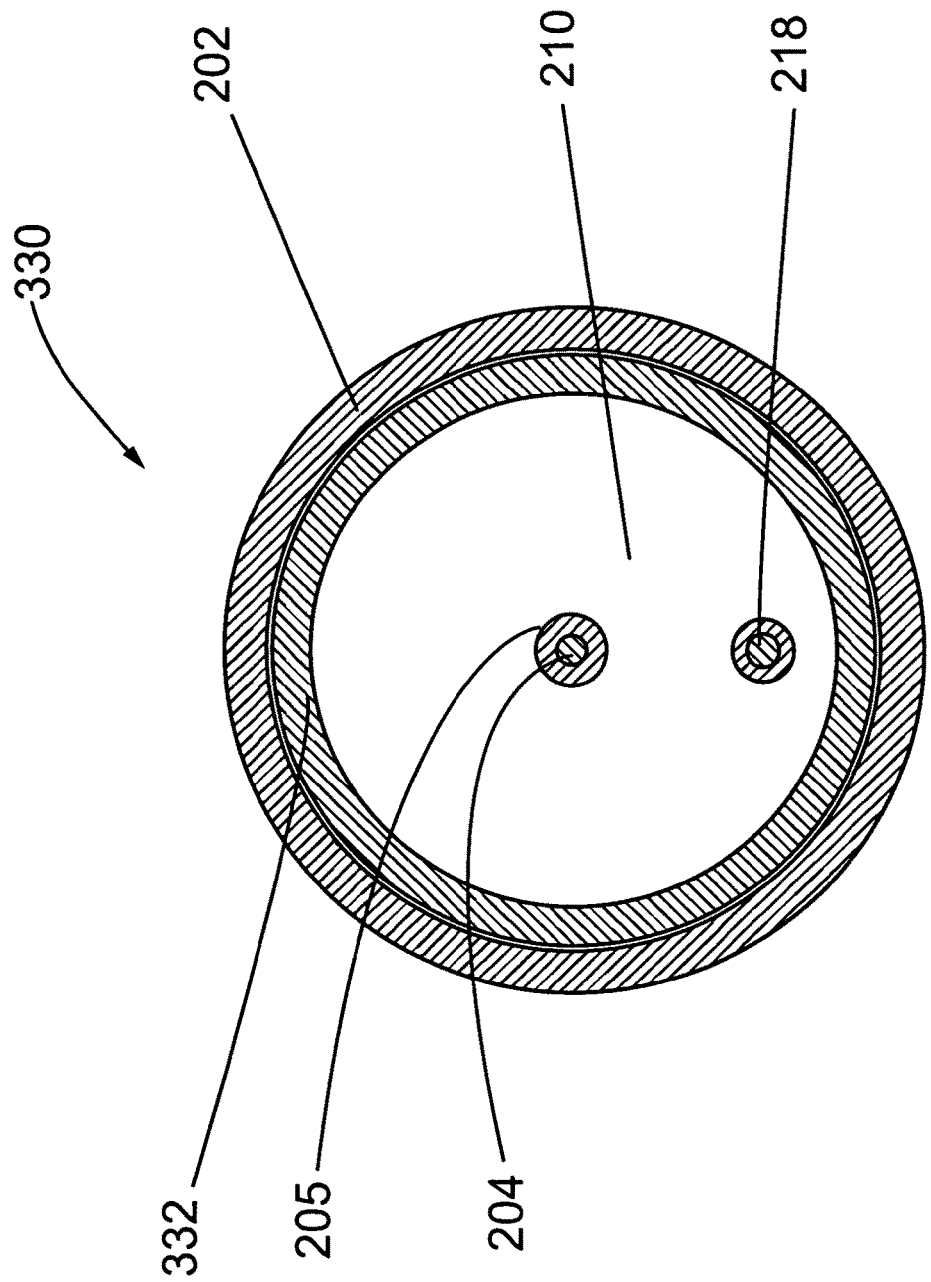
FIG. 19 is a cross section view of the probe shown in FIG. 17 along the line 19-19.

FIG. 17 shows an embodiment of a probe 330 in which a two lumen catheter is used with the grounding electrode comprised of a ring electrode 332 that fits inside sheath 202 in the proximal back section adjacent to the distal front section. This ring electrode 332 may be composed of, but not limited to: metals such as stainless steel, brass, or copper. It may also be machined from plastics such as polymethylmethylacrylate (PMMA), polyetheretherketone (PEEK), polymide, or polycarbonate that may be machined and then subsequently coated with a metal such as gold, chrome, or silver. This ring electrode 332 is connected to ground by ground electrode 238 that is insulated over a portion of its length. In this embodiment, the grounding wire 238 is placed underneath the ring electrode such that the ring electrode 332 allows both electrical coupling and precise positioning of the grounding electrode 238. The ring electrode 332 may also be machined such that it contains a rigid extension that serves as the grounding electrode. FIG. 18 is a cross section of the FIG. 17 along the line 18-18. FIG. 19 is a cross section of the FIG. 17 along the line 19-19.

Figure 20:
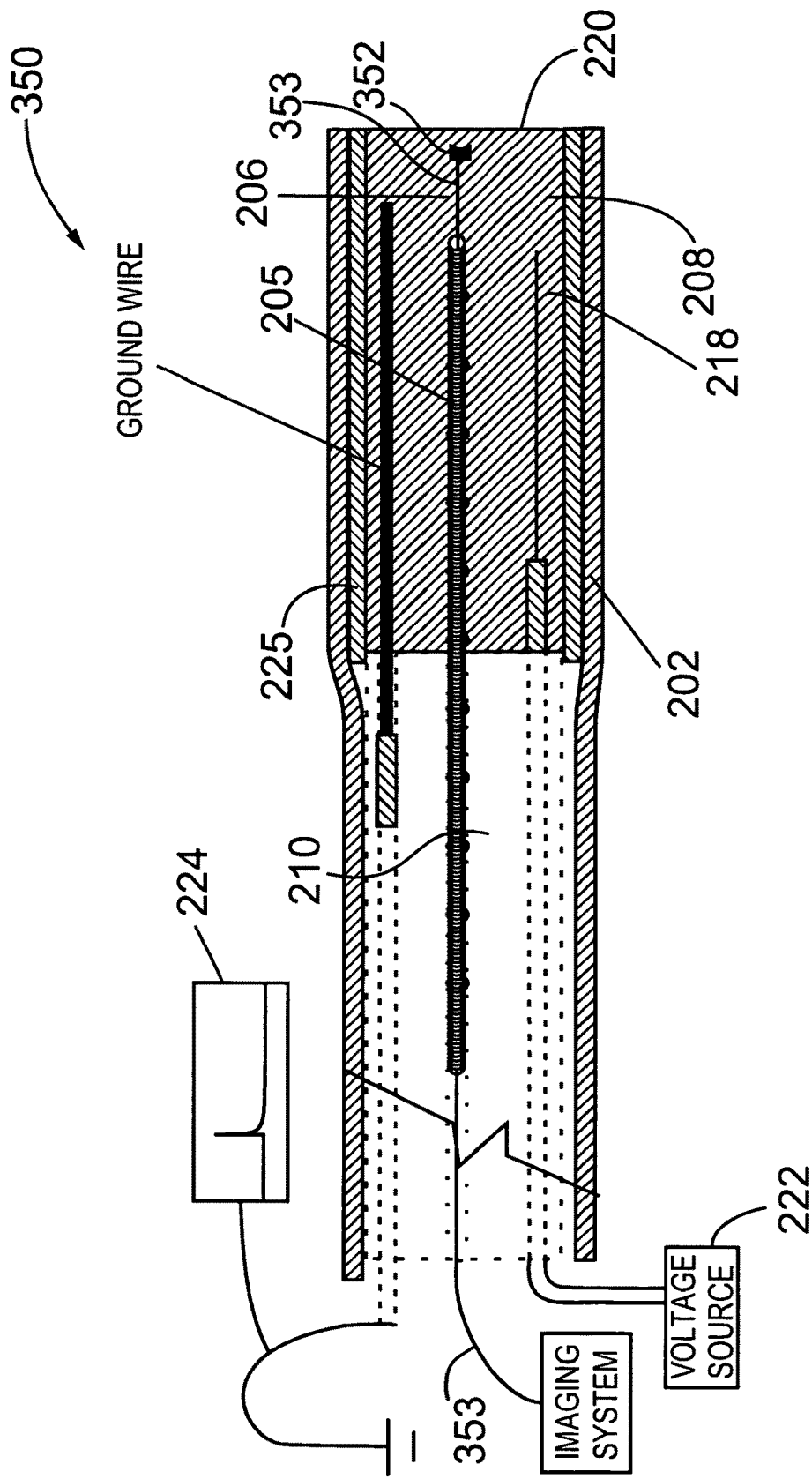
FIG. 20 is a cross sectional view of another embodiment of an imaging probe in which a three lumen dissipative polymer catheter is employed with a forward directed ultrasound transducer.

FIG. 20 shows an embodiment of a probe 350 in which the imaging means 206 includes forward-facing ultrasound transducer 352 that is affixed to the distal end of a microcoaxial cable 353 which is connected to the ultrasound imaging system electronics This transducer 352 is capable of transmitting and receiving ultrasound energy. Thus, when combined with the electrostatic scanning mechanism described herein, two dimensional ultrasonic imaging is possible. It will be appreciated that shaping the end face of the transducer 352 may be employed for optimal ultrasound focusing.

Figure 21:
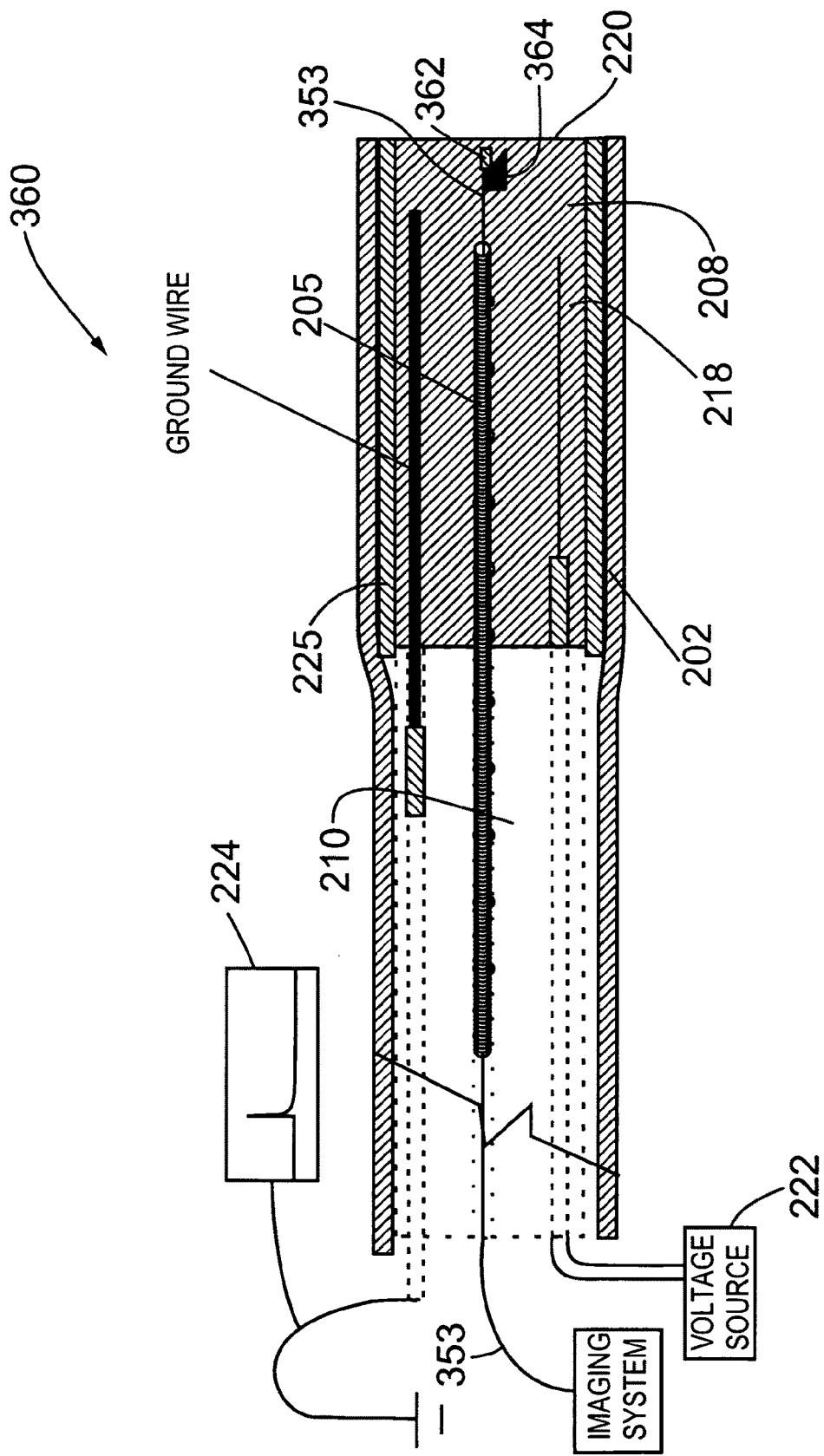
FIG. 21 is a cross sectional view of another embodiment of an imaging probe in which a three lumen dissipative polymer catheter is employed with a side directed ultrasound transducer that is coupled to a prism or mirror to redirect the ultrasound energy towards the front of the probe.

FIG. 21 shows an embodiment of a probe 360 in which a more conventional side-directed ultrasound transducer 362 is coupled to a reflective prism or mirror like object 364 to direct the ultrasound energy forward. This prism or mirror 364 may be composed of, but not limited to, steel, brass, or glass.

A three lumen catheter that was used in the optical coherence tomography imaging experiments with the results shown in FIGS. 24, 25 and 26 discussed hereinafter. The catheter was 1.8 mm in diameter with a 400 micron central lumen to house the cantilever and 300 micron peripheral lumens to contain the electrodes. The catheter was extruded using Arkema Pebax 7233 SA01.

Figure 22:
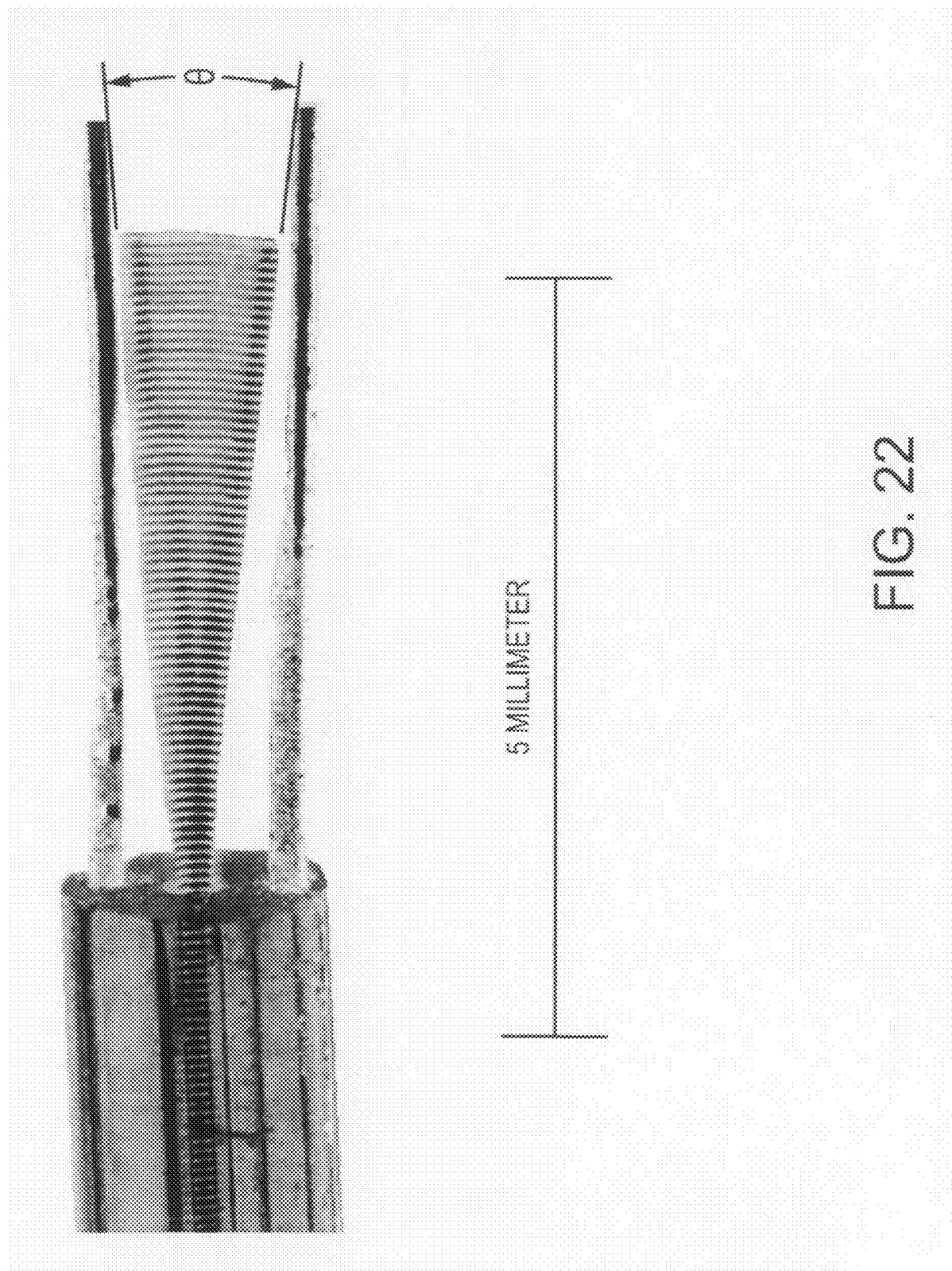
FIG. 22 is a photograph of an embodiment of the scanning probe in motion.

An image of the cantilever probe in motion was taken using a low magnification stereomicroscope and is shown in FIG. 22. In this case, an electrical potential of 1700 Volts with 5 micro ampere current was applied as a driving voltage using a power supply that was current limited at 20 micro amperes. A thirteen (13) degree angle of oscillation was measured in software and is labeled in FIG. 22 as θ. The probe used two electrodes in one electrode was grounded while the other electrode was held at a constant voltage of 1700 V. The electrodes both possess exposed regions which allow for electrical contact with the cantilever. A 60 micron optical fiber was contained within the oscillating metallic coil. The 60 micron diameter optical fiber was obtained by etching a stand 125 micron fiber in an acid. In this case the coil was composed of platinum. This design used to oscillate the cantilever is very similar to the embodiment shown in FIG. 13.

Figure 23:
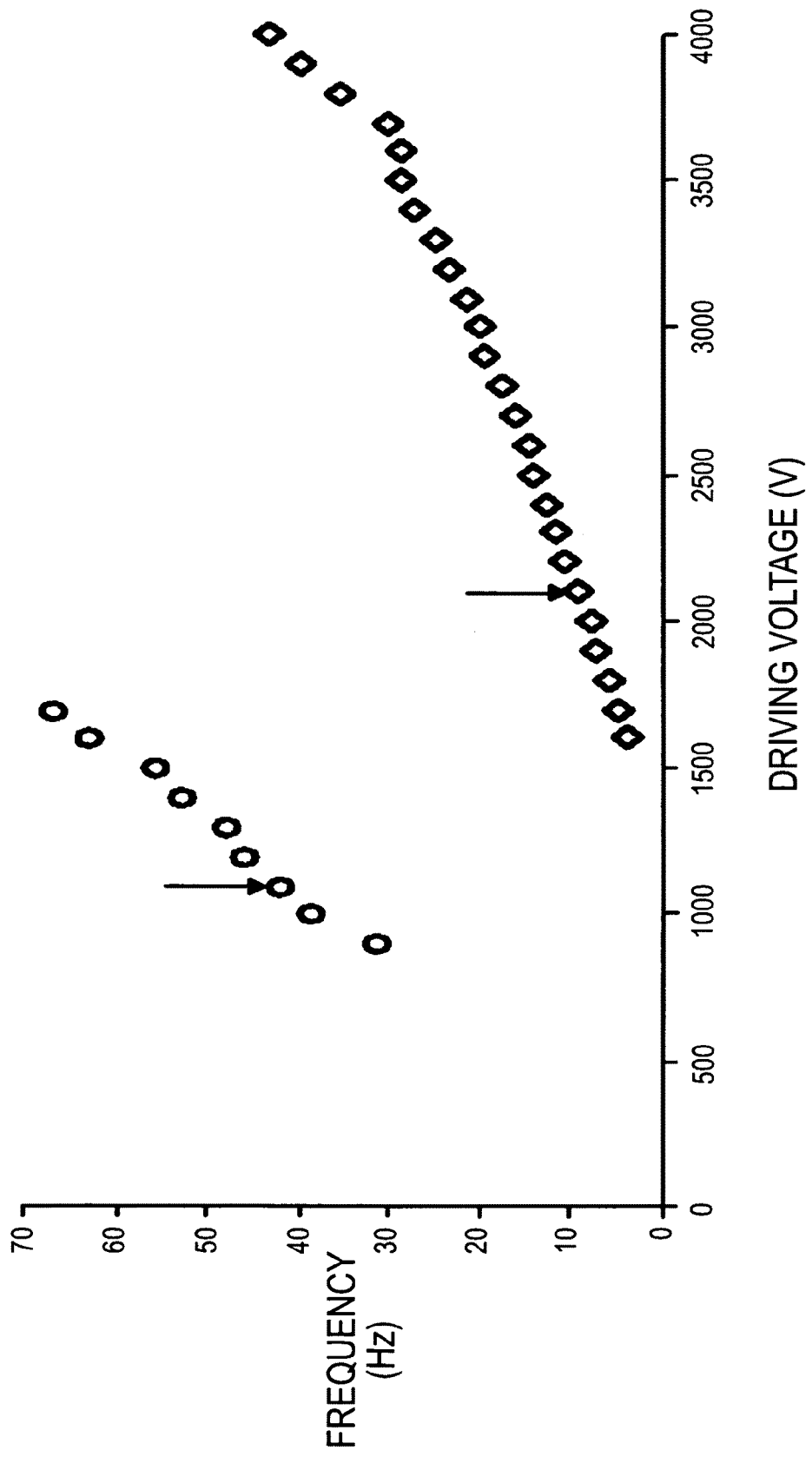
FIG. 23 is a graph of the frequency of oscillation of the cantilever as a function of driving voltage applied for motion in two different media: oil (shown with diamonds) and air (shown with circles)

FIG. 23 shows a calibration plot for the frequency of oscillation of the cantilever in a configuration similar to that shown in FIG. 13 and FIG. 22. We plot the frequency of oscillation when the cantilever is placed in either mineral oil (diamonds) or air (circles). The oscillation rate was measured using the frequency of the trigger signals that were measured on an oscilloscope. Note that a certain driving voltage is required to commence motion of the cantilever. This voltage is marked with arrows on the graph. Once motion is started, however, the voltage can be decreased and the cantilever will oscillate at a slower rate corresponding to the decreased driving voltage.

FIG. 24 shows OCT images taken with a probe similar to that shown in FIG. 13. In the embodiment of the imaging probe used to acquire the optical coherence tomography images a ball lens was affixed to a 60 micron optical fiber. The fiber was attached to the sample arm of a commercially available OCT system and scanning of the cantilever was initiated by activating the high voltage power source. An OCT image of an arterial phantom mimicking a nearly occluded vessel is shown in FIG. 24A with the corresponding photograph in FIG. 24B. Walls of the phantom are labeled "W" and the channel is identified with an arrow in both FIG. 24A and FIG. 24B.

Figure 24A:
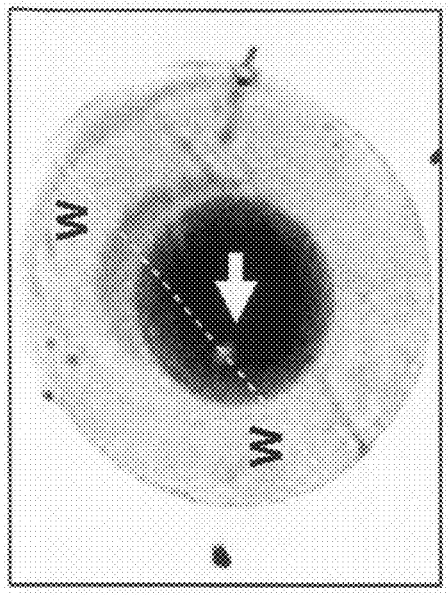
FIGS. 24A-24C show examples of optical coherence tomography images acquired using an embodiment of the probe with a ball lens.
Figure 24B:
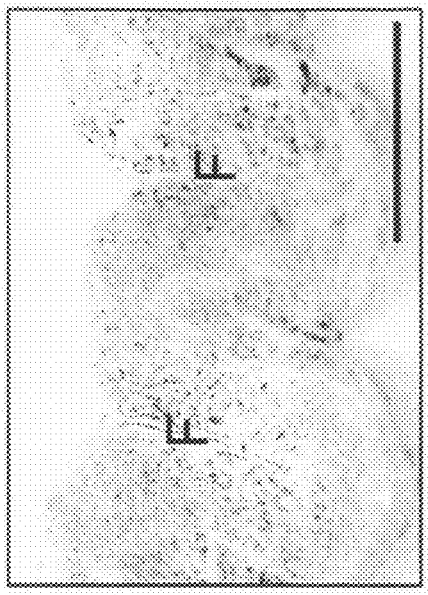
Figure 24C:
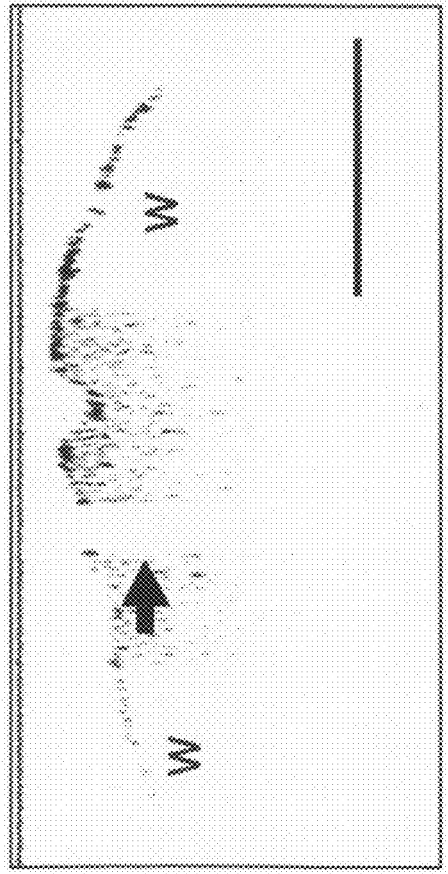
Figure 24D:
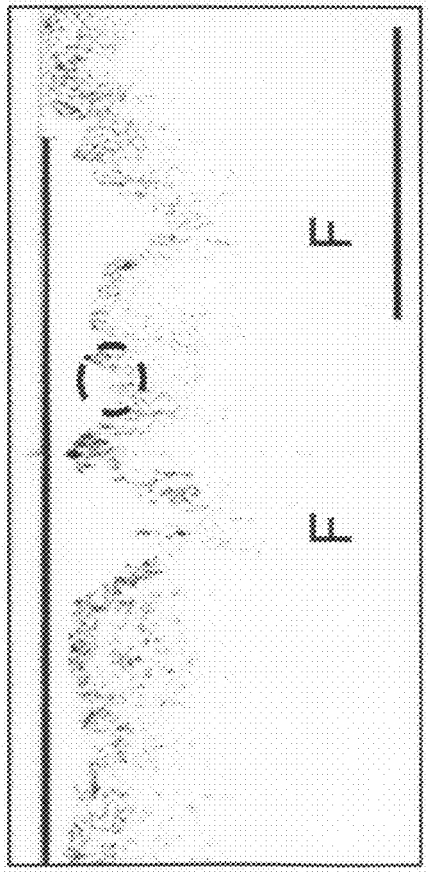
FIG. 24D shows a white light image of a piece of excised rabbit colon.

The arterial occlusion phantom was created by mixing titanium dioxide powder into a poly(dimethylsiloxane) (PDMS) polymer prior to curing; this mixture was then allowed to cure inside a piece of tygon tubing; a wire was also placed in the tygon tubing to form a small channel that is seen on the OCT image. An OCT image of a formalin-fixed rabbit colon is shown in FIG. 24C with a corresponding white light picture shown in FIG. 24D. A dashed circle identifies a crypt-like object seen in the OCT image while the letter "F" is used to denote fissures. Scale bars represent 1 mm.

Figure 25A:
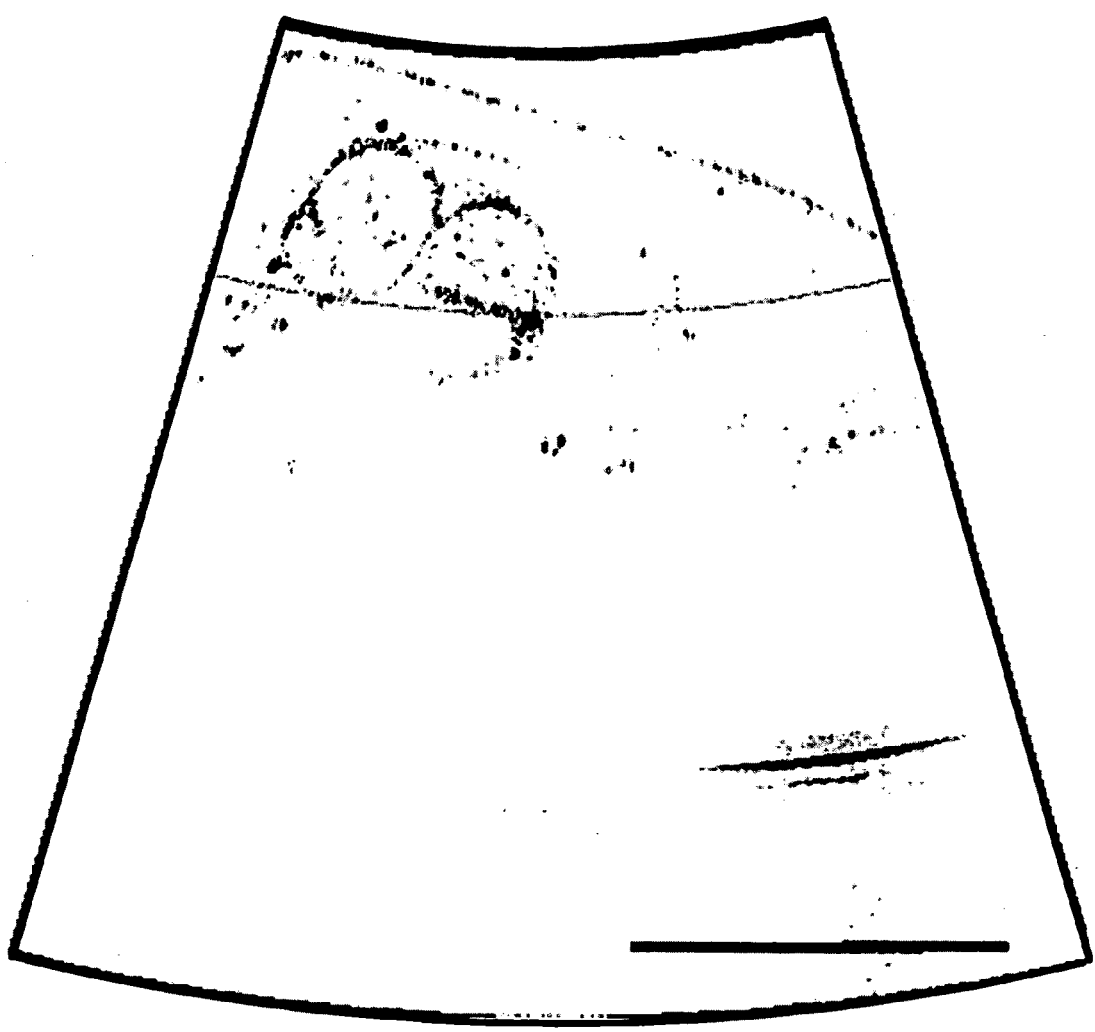
Figure 25B:
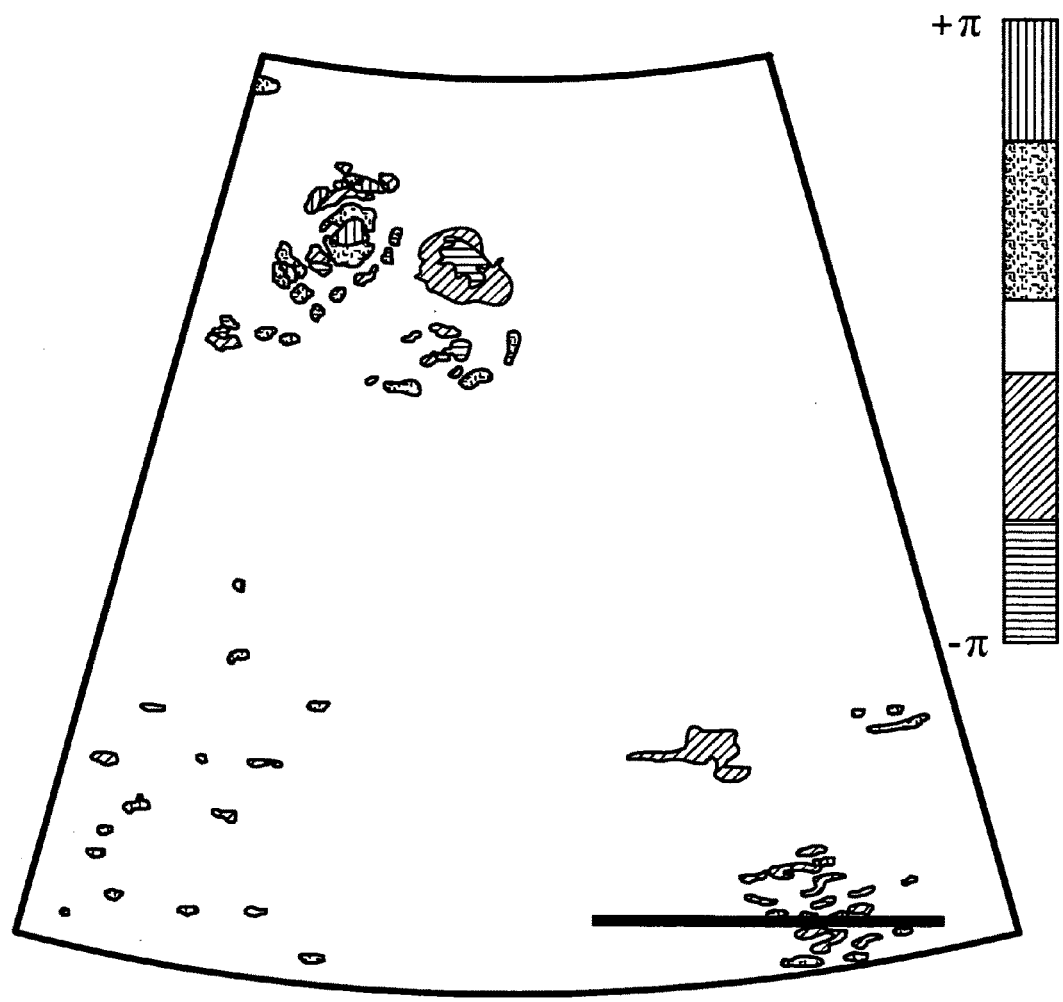
FIG. 25B shows a Doppler flow map of the tadpole heart.

FIGS. 25A and 25B demonstrate the use of an electrostatic imaging probe similar to that shown in FIG. 14 to image a stage 45 *Xenopus Laevus* (African frog) embryo in vivo. FIG. 25A shows a structural image while FIG. 25B shows a processed Doppler image of the blood flow in the heart of the *Xenopus Laevus*. In these images the probe was driven with 1700 V at an oscillation frequency of 5 Hz. This imaging speed allowed for sufficient signal to noise to allow for Doppler imaging. Scale bars in the image represent 1 mm.

Figure 26:
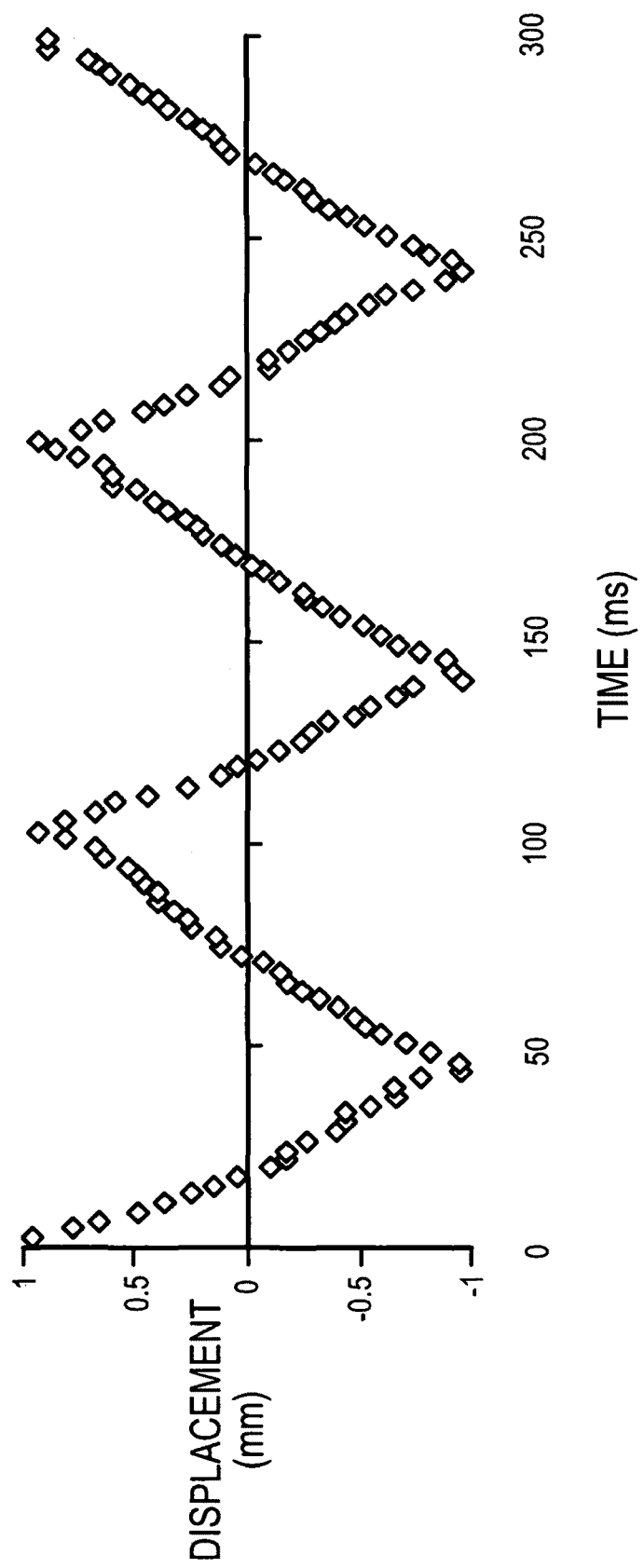
FIG. 26 shows a plot of the vertical displacement of the tip of cantilever as function of time for a driving voltage of 2100 V in oil.

FIG. 26 illustrates motion characterization of the vertical displacement of the cantilever tip as a function of time when driven at 2100 V in mineral oil. The design used to perform this calibration is very similar to the embodiment shown in FIG. 13 and the oscillating probe shown in FIG. 22. The position of the end tip of the cantilever was imaged using a high speed camera with a frame rate of 454 frames per second; commercially available motion tracking software was used to track the position of the end tip of the cantilever.

Figure 27:
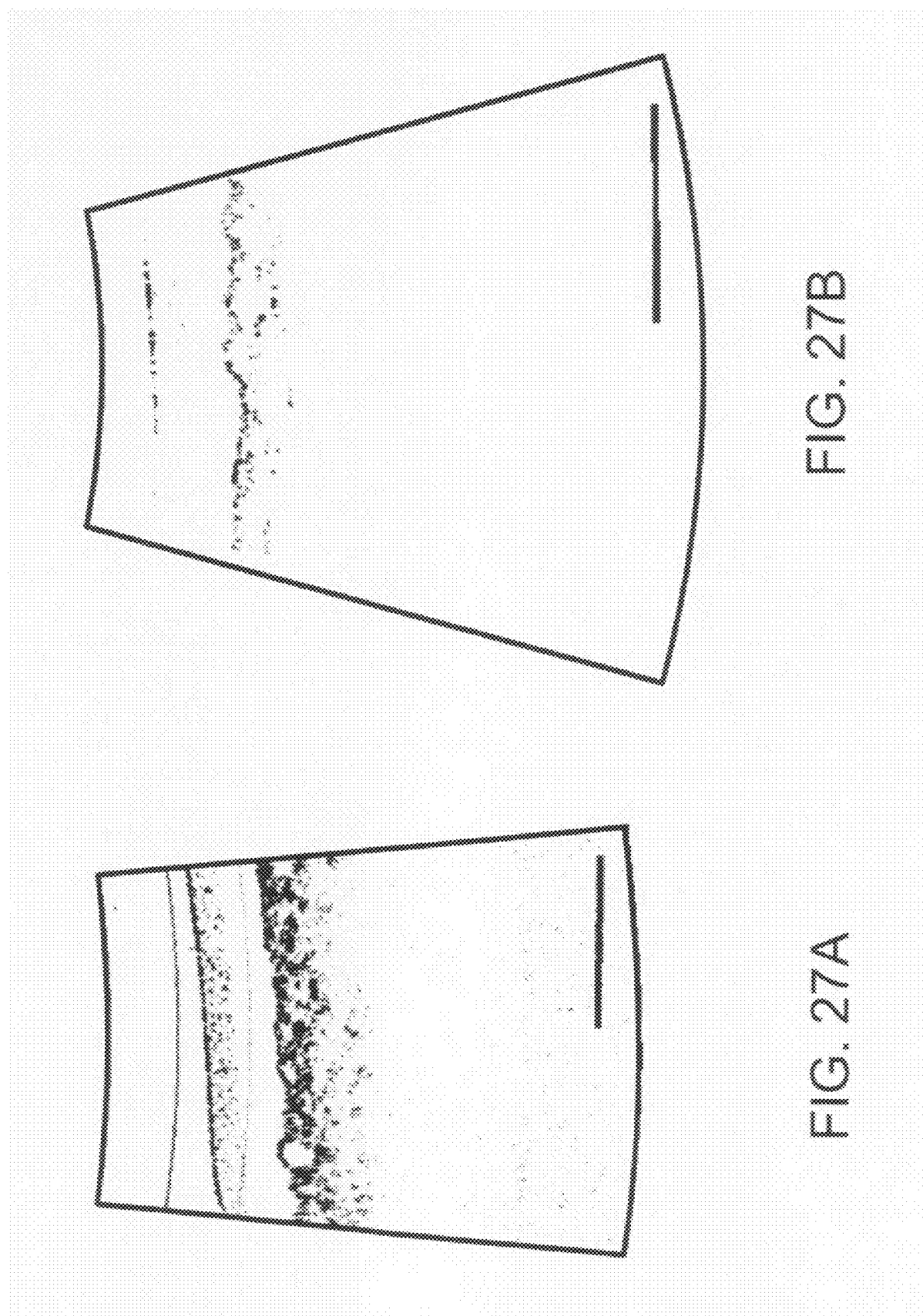
FIGS. 27A and 27B compare optical coherence tomography images taken using two different embodiments of the probe of an IR detection card.

FIGS. 27A and 27B show a comparison of OCT images taken with two different probe designs. The image in FIG. 27A shows an OCT image of an IR card taken with a design similar to that shown in FIG. 13 while the image in FIG. 27B shows was taken with a design similar to FIG. 14. Of importance to note is the increase in the angular field of view in the right hand image by scanning the fiber proximal to the GRIN lens. The left image has an angular field of view of 13 degrees while the right image has an angular field of view of 33 degrees. Scanning the optical fiber in front of the GRIN lens does however does introduce more image artifacts in the image. Scale bars represent 1 mm.

Figure 28:
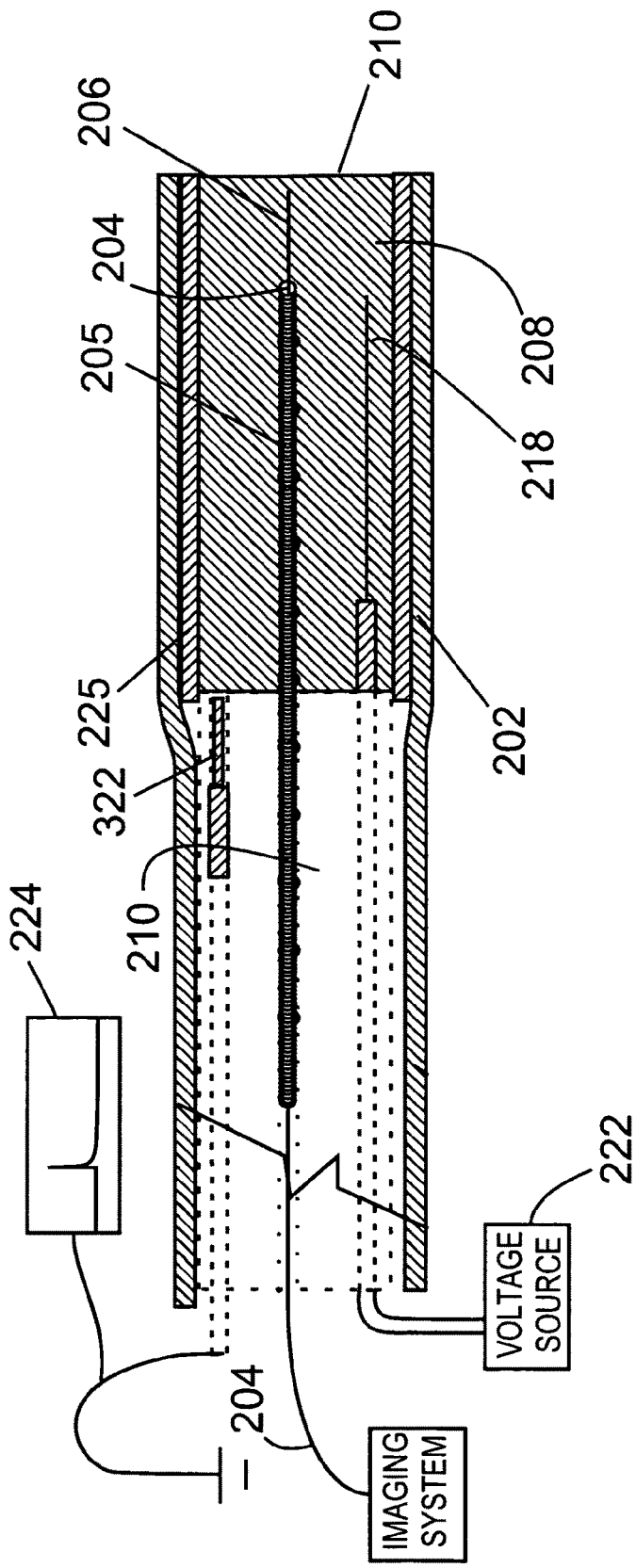
FIG. 28 is an alternative embodiment that shows the ground conductor withdrawn inside a three lumen catheter.

FIG. 28 illustrates an embodiment of an electrostatically driven imaging probe in which the grounding electrode 322 is located only inside the lumen of the dissipative polymer catheter 210 in the proximal back section of the probe. The grounding electrode 322 possesses an uninsulated length which is conductive that only contacts the dissipative polymer in the distal back section of the catheter. This grounding electrode 322 thus serves to indirectly couple the coil 205 to ground through the dissipative polymer. This conductor may or may not be sealed off from the media 208. By being short enough so that it is not in direct conduct with the media 208 located in the distal front section of the probe, more conductive or polar media may be used in the distal front section of the probe without resulting in electrolysis of the media. It was observed that when a polar media was used in the probe design and the ground electrode was contained within the media as in FIG. 15, that bubbles were produced. Withdrawing the grounding electrode inside the proximal back section of the probe resulted in a slower oscillation rate, but without the production of bubbles inside the media 208.

Figure 29:
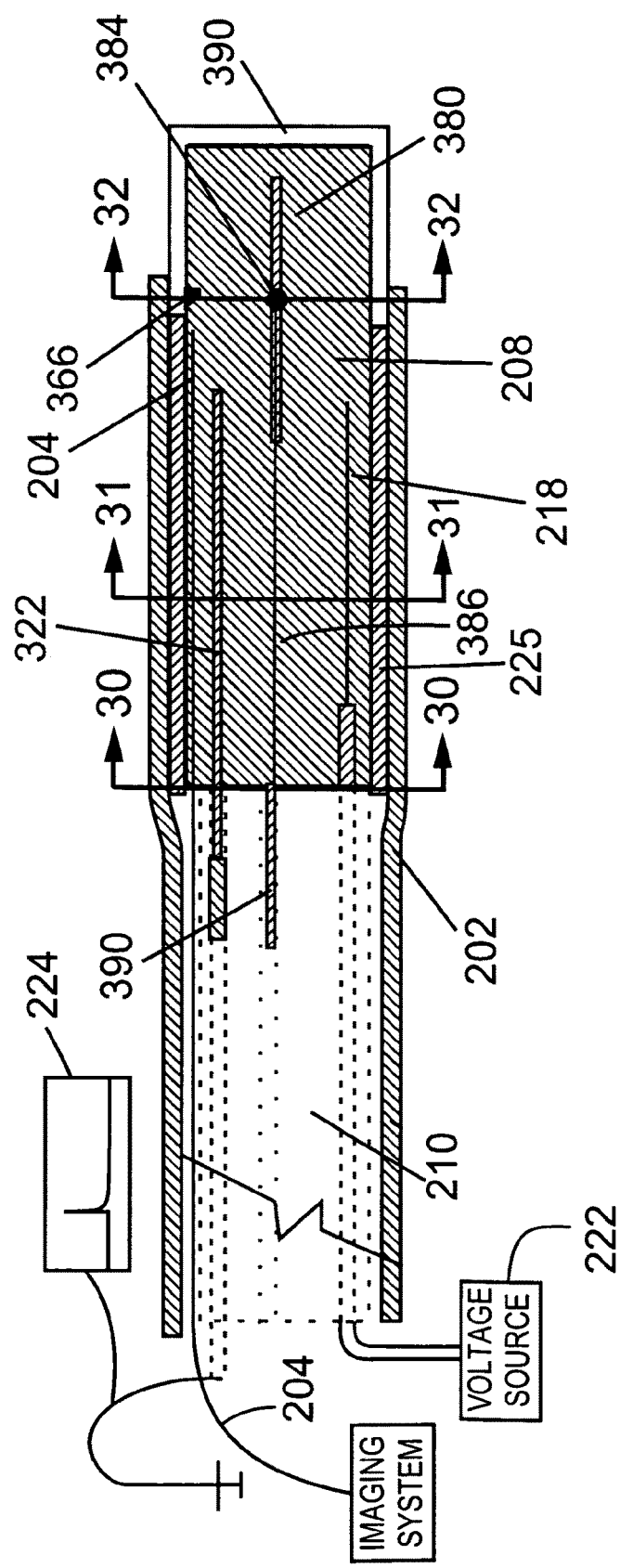
FIG. 29 is an embodiment of the imaging probe in which a mirror is scanned inside the catheter.
Figure 30:
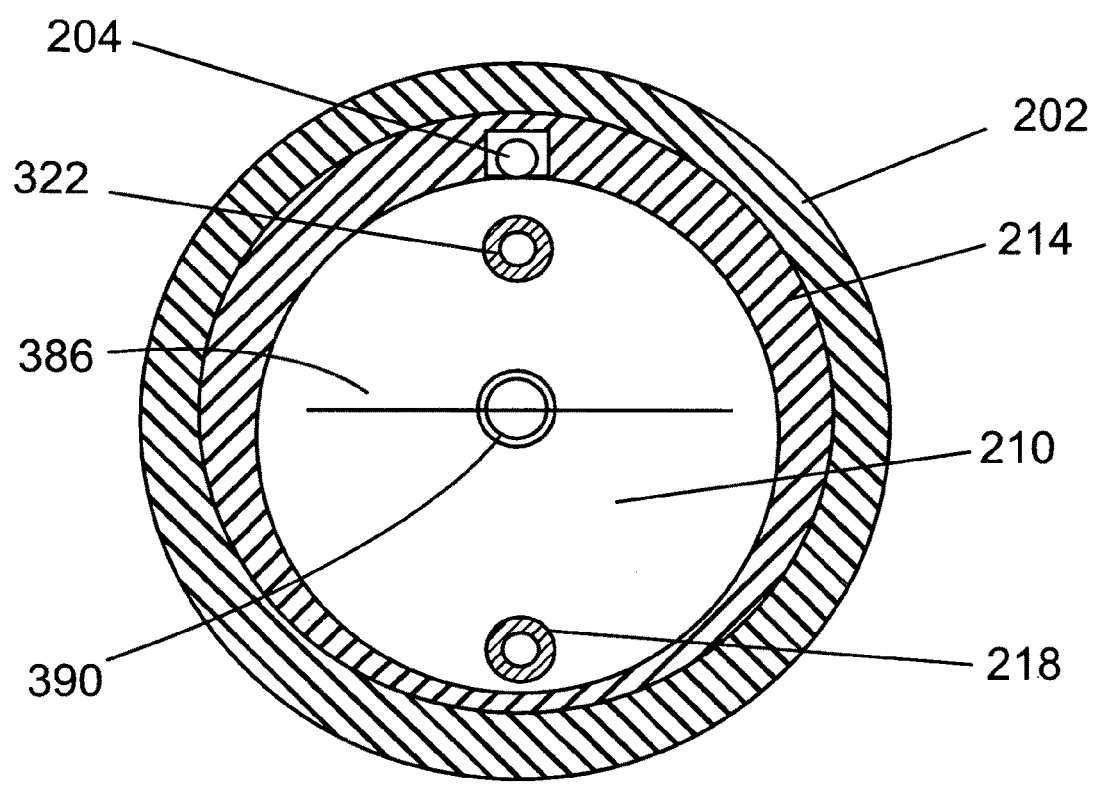
FIG. 30 is a cross section of FIG. 29 along the line 30-30.
Figure 31:
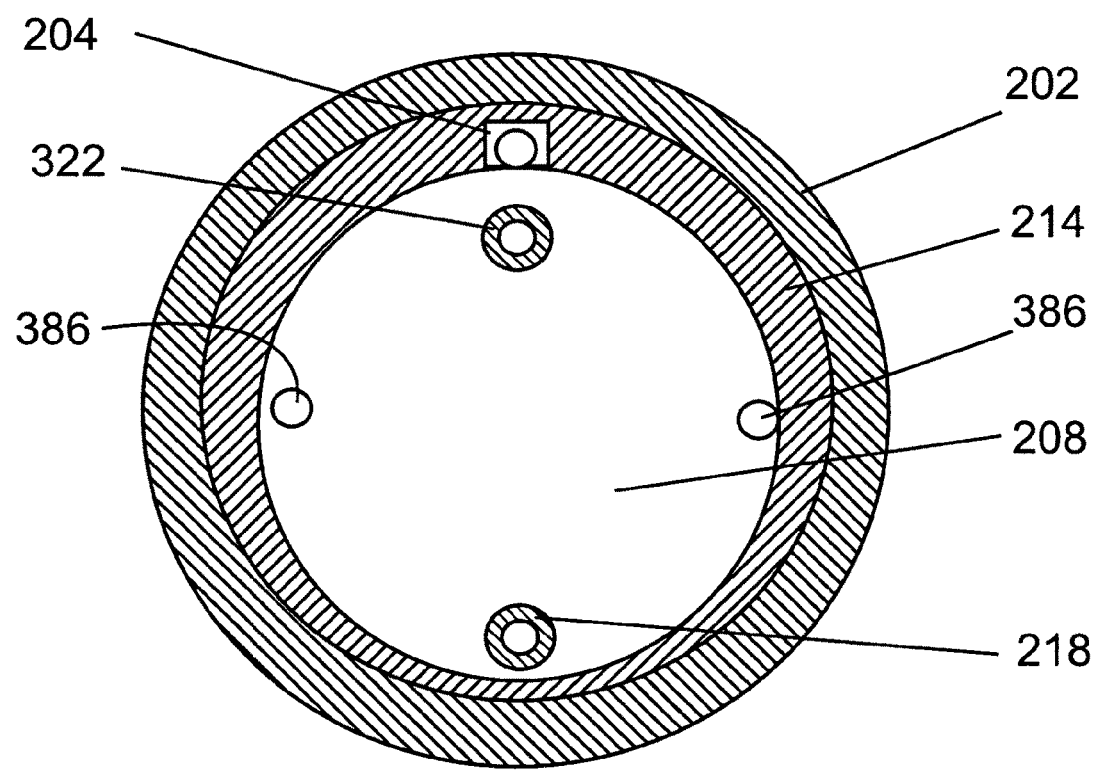
FIG. 31 is a cross section of FIG. 29 along the line 31-31.
Figure 32:
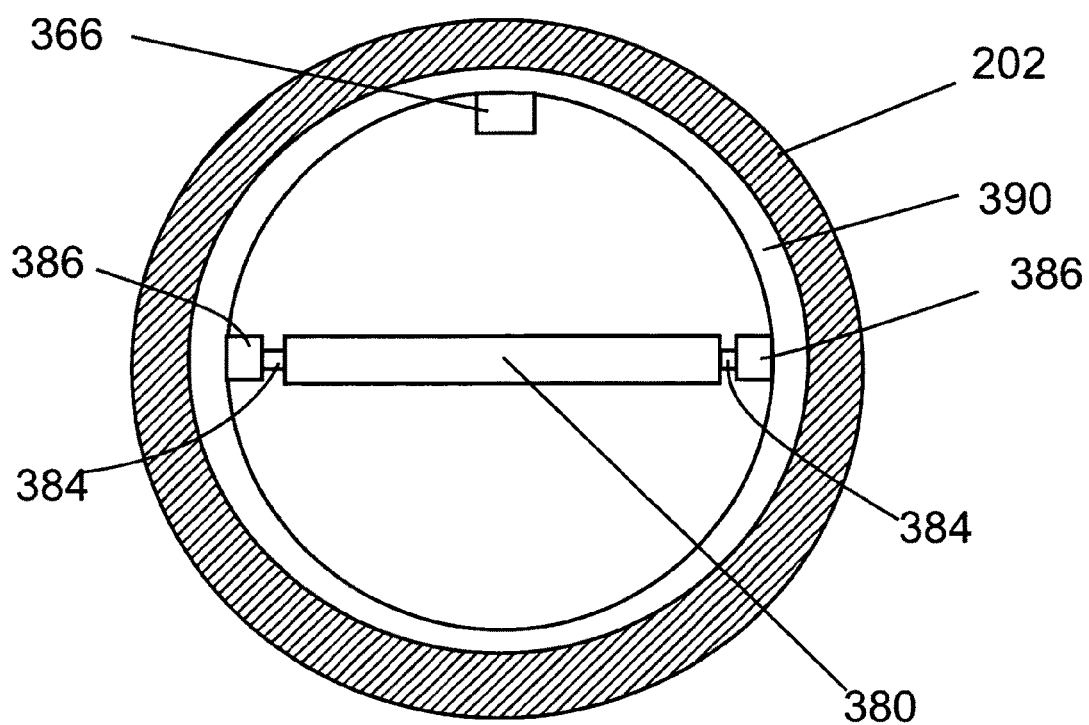
FIG. 32 is a cross section of FIG. 29 along the line 32-32.

FIG. 29 illustrates an embodiment of an electrostatically driven imaging probe in which the cantilever is replaced by a reflecting disk 380. This reflecting disk 380, may be reflective to both ultrasound and/or optical energy. The reflecting disk 380 is pivotally mounted on a pivoting pin 384, that allows the disk 380 to rotate and thus alter its angle. The disk 380 is electrically connected to the pivoting pin 384, by producing both the disk 380 and the pin 384 using metal conductors. The pivoting pin 384 in turn, is connected to a wire 386 that connects to a conductive segment 390 contained within a lumen of the dissipative polymer in volume 210. Thus the reflecting disk 380 is electrically connected to the conductive segment 390. This conductive segment 390 is coupled to the ground electrode 322 through the dissipative polymer in section volume 210.

Thus the reflecting disk 380 is indirectly coupled to ground through the dissipative polymer in volume 210. Upon activation of the high voltage from the high voltage source 222 the reflecting disk 380 is attracted to the high voltage electrode 218. This attraction results in the disk 380 pivoting about the pivoting pin 384 such that the proximal edge touches the electrode, 218. Upon contact, the reflecting disk 380 acquires charge of the same polarity as the high voltage electrode 218 and thus repels. This repulsion results in the disk 380 pivoting about the pin 384 such that the proximal edge touches the ground electrode 322.

Upon contract with the ground electrode 322 the disk 380 loses its acquired charge and may once again be attracted towards the high voltage electrode 218. The imaging conduit 204 in this embodiment, is placed above the grounding electrode 322. A beam directing element 366 causes the energy emitted from the imaging conduit 204 to be reflected towards the disk 380. Finally an end cap 390 capable of transmitting optical and ultrasonic energy is located on the distal end of the probe that serves to seal the distal front section of the catheter.

The different embodiments of the imaging probe disclosed herein and the various components they are made from may span several different dimensions and properties depending on the anatomic location and application of the imaging probe. For example, for use in the cardiovascular system, including the cardiac chambers, the imaging probe would be elongate and flexible, with a length ranging from about 5 to about 2000 mm, preferably with a length ranging from about 300 mm to about 1500 mm. The imaging conduit and imaging assembly may have a maximum cross-sectional dimension ranging from about 200 microns to about 10 mm, preferably ranging from about 500 microns to 5 about mm. The imaging conduit and imaging assembly are surrounded by an external sheath. This enables the imaging conduit 204 (FIG. 1B) and imaging assembly to rotate within the external sheath while mechanically isolating the rotational motion of these two components from the surrounding tissues.

In yet another example, the use of the imaging probe in the gastrointestinal system would typically have the imaging probe being elongate and flexible, with a length ranging from about 100 mm to about 2000 mm and preferably in the range of about 300 mm to about 1500 mm. The maximum cross-sectional dimension would typically range from about 3 mm to about 20 mm.

In yet another example, the use of the imaging probe to image soft tissue via percutaneous means would require the imaging probe include a rigid shaft, rather than flexible as for the aforementioned applications. Thus the external sheath would be replaced by a rigid hollow shaft, such as a stainless steel tube. The length of the shaft would be from about 1 to about 12 cm.

As mentioned previously, Boppart et al. (U.S. Pat. No. 6,485,413) discloses an electrostatic-based actuator for forward-viewing optical coherence tomography in which the cantilever is directly connected to ground or enabled with an electrostatic slide. The direct connection to ground results in significant electrostatic discharge given the high voltage necessary to oscillate a rigid fiber. By coupling the cantilever to ground through a dissipative polymer such as disclosed in the present application circumvents this problem. Furthermore the Boppart et al. discloses the use of a time varying electrical field in order to produce an oscillatory motion. By using a dissipative polymer to couple the cantilever to ground in the present application allows production of oscillatory motion with both constant voltage as well as time varying driving voltages.

The electrostatic scanning motion described in this work can be used in conjunction with a torque cable as described by Crowley et al. in U.S. Pat. No. 5,372,138 (which is incorporated herein by reference in its entirety) to extend the scanning motion to cover a two dimensional scanning field by rotating the probe while the cantilever is scanning. In such an embodiment a torque cable may be placed over the dissipative polymer in volume 210 causing the cantilever, and the electrode(s) 218 to rotate inside the sheath 202 (FIG. 1A).

Alternatively the torque cable may be placed over the outer sheath 202 such that the entire imaging probe rotates at the same time as the cantilever scans. This rotational driving torque would be provided by a motor external to the catheter. This rotational torque would be coupled into the catheter through an element generally labeled as an adaptor 14 in FIG. 1A. This adaptor 14 would include an electrical slip ring to allow electrical connections be preserved in the rotating catheter. It may also include a fiber optic rotary joint to allow optical connections to be maintained while the probe rotates. The goal of this rotation is to allow multiple different angles for the cantilever to scan.

It will be appreciated by those skilled in the art that the scanning cantilever disclosed herein may be used as a switching means in non-medical applications such as, but not limited to, optical networks, electrical switching, optical switching, and mechanical switches.

As used herein, the terms "comprises", "comprising", "includes" and "including" are to be construed as being inclusive and open ended, and not exclusive. Specifically, when used in this specification including claims, the terms "comprises", "comprising", "includes" and "including" and variations thereof mean the specified features, steps or components are included. These terms are not to be interpreted to exclude the presence of other features, steps or components.

The foregoing description of the preferred embodiments of the invention has been presented to illustrate the principles of the invention and not to limit the invention to the particular embodiment illustrated. It is intended that the scope of the invention be defined by all of the embodiments encompassed within the following claims and their equivalents.

Therefore what is claimed is:

1. Electrostatically driven imaging probe, comprising:
  a) an elongate hollow catheter sheath having distal front and back sections and an elongate proximal section and having a diameter suitable to permit insertion of the elongate hollow catheter sheath into bodily lumens and cavities, the distal back section containing an electrically dissipative polymer sealed therein which is wrapped by a metal coil for connection to ground potential and a timing circuit;
  b) imaging means located in said distal front section for emitting energy and receiving energy reflected back from interior surfaces of said bodily lumens and cavities, said distal front section containing one of a medium and vacuum sealed therein which allows transmission of imaging energy emitted by the imaging means, said imaging means being connected to an imaging conduit which extends through a proximal end of the elongate hollow catheter sheath for connection to an image processing and display system, said imaging conduit being enveloped by metal and a portion of the metal enveloped imaging conduit in the distal front section forming a cantilever; and
  c) an elongate electrode located in the elongate hollow catheter sheath having an elongate uninsulated electrode section located in said front distal section, the elongate electrode being connected to a high voltage power supply, wherein in operation when a high voltage is applied to the elongate electrode the cantilever is electrically attracted to the elongate uninsulated electrode section and undergoes deflection towards the elongate uninsulated electrode section and upon contacting the elongate uninsulated electrode section the portion of the metal enveloped imaging conduit in the distal front section acquires an electrical charge from the elongate uninsulated electrode section thereby causing the metal enveloped imaging conduit in the distal front section to be repelled therefrom thereby causing the imaging means to scan the field of view.

2. The electrostatically driven imaging probe according to claim 1 wherein said imaging conduit is an optical fiber and wherein said imaging means includes optical radiation emitted from an end portion of said optical fiber located in said distal front section, said optical fiber being optically coupled to a source of optical radiation through said proximal end of the elongate hollow catheter sheath.

3. The electrostatically driven imaging probe according to claim 2 wherein said imaging means includes focusing optics located in a distal end portion of said distal front section for directing and focusing light emitted from said optical fiber and collecting light reflected back into said distal front section.

4. The electrostatically driven imaging probe according to claim 3 wherein said focusing optics includes a GRIN lens mounted in the distal end portion of said distal front section.

5. The electrostatically driven imaging probe according to claim 3 wherein said focusing optics includes a ball lens attached to end portion of said optical fiber.

6. The electrostatically driven imaging probe according to claim 3 wherein said focusing optics includes an axicon lens attached to the end portion of said optical fiber.

7. The electrostatically driven imaging probe according to claim 1 wherein said imaging means is an ultrasound transducer located in said distal front section for emitting ultrasound signals and detecting reflected ultrasound signals, and wherein said imaging conduit is a coaxial electrical cable electrically connected to said ultrasound transducer at one end and to a power supply through said proximal end of the elongate hollow catheter sheath at another end thereof.

8. The electrostatically driven imaging probe according to claim 7 wherein said ultrasound transducer has a shaped end face for focusing the emitted ultrasound signals.

9. The electrostatically driven imaging probe according to claim 1 including a ground electrode having an uninsulated section located in one or both of said distal front and back sections connected to said electrical ground potential wherein when said cantilever comes into physical contact with said ground electrode it quickly dissipates all of its acquired charge upon contact and is therefore immediately available to be attracted to the elongate electrode once again so that said cantilever can undergo rapid oscillation.

10. The electrostatically driven imaging probe according to claim 9 wherein said uninsulated section of said ground electrode is located solely inside said dissipative polymer such that it is not in direct contact with said media in the distal front section.

11. The electrostatically driven imaging probe according to claim 9 wherein said uninsulated section of said ground electrode is located solely inside said distal front section.

12. The electrostatically driven imaging probe according to claim 9 wherein said uninsulated section of said ground electrode is located in both said distal front and back sections.

13. The electrostatically driven imaging probe according to claim 1 including a rotational drive mechanism such that both the distal front and back sections of the electrostatically driven imaging probe are rotated such that the scanning of the cantilever encompasses a two dimensional area in said bodily lumens and cavities in front of said distal front section.

14. The electrostatically driven imaging probe according to claim 1 including at least one additional elongate electrode located in said distal front section connected to said high voltage power supply.

15. The electrostatically driven imaging probe according to claim 14 wherein said high voltage power supply is configured to apply time varying electrical potentials independently to said elongate electrode and to said at least one additional elongate electrode to give a desired scanning motion of the cantilever.

16. The electrostatically driven imaging probe according to claim 15 wherein said high voltage power supply is configured to hold any one of said elongate electrode and said at least one additional elongate electrode at ground potential.

17. The electrostatically driven imaging probe according to claim 15 wherein said at least one additional elongate electrode is three (3) additional elongate electrodes each connected to said high voltage power supply.

18. The electrostatically driven imaging probe according to claim 1 wherein said dissipative polymer is selected from the group consisting of antistatic molecules blended with polymers, and conductive particles blended with conventional insulating polymers.

19. The electrostatically driven imaging probe according to claim 1 wherein said dissipative polymer is Polyamide/Polyether Block Copolymer (Pebax)™.

20. The electrostatically driven imaging probe according to claim 1 wherein said medium sealed in said distal front section is a fluid.

21. The electrostatically driven imaging probe according to claim 20 wherein said medium sealed in said distal front section is a fluid having a pre-selected viscosity for damping oscillatory motion of the cantilever to give pre-selected scanning speeds.

22. Electrostatically driven imaging probe, comprising:
a) an elongate hollow catheter sheath having distal front and back sections and an elongate proximal section and having a diameter suitable to permit insertion of the elongate hollow catheter sheath into bodily lumens and cavities, the distal back section containing an electrically dissipative polymer sealed therein which is wrapped by a metal coil which is connected to ground potential and a timing circuit;
b) imaging means located in said distal front section for emitting energy and receiving energy reflected back from interior surfaces of said bodily lumens and cavities, said distal front section containing one of a medium and vacuum sealed therein which is transparent to said energy emitted by the imaging means, said imaging means being connected to an imaging conduit which extends through a proximal end of the elongate hollow catheter sheath for connection to an image processing and display system;
c) a conductive, reflective disc pivotally mounted about a pivot axis in said front distal section and electrically coupled to said electrically dissipative polymer, said reflective member being positioned to receive and reflect said energy from said imaging means, and to receive and reflect said energy reflected back from interior surfaces of said bodily lumens and cavities back to said imaging means;
d) a ground electrode having an uninsulated section located in said distal front section connected to said electrical ground potential; and
e) an elongate electrode located in the elongate hollow catheter sheath having an elongate uninsulated electrode section located in said front distal section, the elongate electrode being connected to a high voltage power supply, wherein in operation when a high voltage is applied to the elongate electrode the conductive, reflective disc is electrically attracted to the elongate uninsulated electrode section causing said conductive, reflective disc to pivot about said pivot axis in one direction causing an outer edge off said conductive, reflective disc to tilt towards said elongate electrode and upon contact with said elongate electrode said conductive, reflective disc acquires charge from said elongate electrode causing it to be repelled thereby resulting in the conductive, reflective disc to pivot towards said ground electrode, and upon contact of said conductive, reflective disk with said ground electrode the conductive, reflective disk loses its charge resulting in its ability to once again be attracted to said electrode.

* * * * *